US006034227A

United States Patent [19]

Pecht et al.

[11] Patent Number: 6,034,227

[45] Date of Patent: Mar. 7, 2000

[54] DNA MOLECULE ENCODING A MAST CELL FUNCTION-ASSOCIATED ANTIGEN (MAFA)

[75] Inventors: Israel Pecht, Rehovot, Israel; Marcelo D. Guthmann, Buenos Aires, Argentina; Michael Tal, Kfar Bilu, Israel

[73] Assignee: Yeda Research and Development Co. Ltd., Rehovot, Israel

[21] Appl. No.: 08/722,126

[22] PCT Filed: Apr. 6, 1995

[86] PCT No.: PCT/US95/04258

§ 371 Date: Oct. 8, 1996

§ 102(e) Date: Oct. 8, 1996

[87] PCT Pub. No.: WO95/27734

PCT Pub. Date: Oct. 19, 1995

[51] Int. Cl.[7] .............................. C07H 21/02; C07K 1/00; C12P 21/06; C12N 15/00

[52] U.S. Cl. ........................ 536/23.1; 530/350; 435/69.1; 435/172.3

[58] Field of Search ................................ 435/69.3, 240.1, 435/320.1, 7.1, 172.3, 69.1; 516/23.5, 23.1; 570/388.2, 395, 350

[56] References Cited

U.S. PATENT DOCUMENTS 4,683,135 7/1987 Pecht et al. ............................... 424/85

OTHER PUBLICATIONS

Ortega Sote et al., "A Monoclonal Antibody that Inhibits Secretion from Rat Basophilic Leukemia Cells and Binds to a Novel Membrane Component", Journal of Immunology, vol. 141, No. 12, pp. 324–4332 Dec. 15, 1988.

Ortega et al., "Possible Interactions between the Fc(epsilon) Receptor and a Novel Mast Cell Function–Associated Antigen", International Immunology, vol. 3, No. 4, pp. 333–342 (1991).

Soto et al., 1988, J. Immunol. 141:4324–4332.

Ortega et al., 1991, Internatl. Immunol. 3:333–342.

*Primary Examiner*—Donald E. Adams
*Assistant Examiner*—Jeffrey S. Parkin
*Attorney, Agent, or Firm*—Browdy and Neimark

[57] ABSTRACT

An isolated DNA sequence encoding a mammalian mast cell function-associated antigen (MAFA) is provided. A soluble derivative of the MAFA is obtained by culturing a host cell transformed by a recombinant expression vector comprising a sequence of said DNA encoding a form of soluble MAFA, and may be used for screening potential ligands of the MAFA. The ligands, alone or in combination with the MAFA, may be used in pharmaceutical compositions for the prevention of inflammatory and allergic reactions.

10 Claims, 8 Drawing Sheets

```
   1  CACCCTGCTTACTGTCGTCACTCCCTGCTGAGTGTGAAGGGCGTTGGGTGGAGATGGCCG
   1                                                          M  A  D

  61  ACAACTCTATCTACTCAACATTAGAGCTGCCTGCTGCACCTCGAGTCCAAGATGACTCCA
   4   N  S  I  Y  S  T  L  E  L  P  A  A  P  R  V  Q  D  D  S  R

 121  GATGGAAGGTCAAAGCTGTCTTACACCGACCCTGTGTTTCCTACCTTGTGATGGTGGCTT
  24   W  K  V  K  A  V  L  H  R  P  C  V  S  Y  L  V  M  V  A  L

 181  TGGGGCTTTTGACTGTGATTCTCATGAGTCTACTGTTGTACCAACGGACTCTGTGCTGTG
  44   G  L  L  T  V  I  L  M  S  L  L  L  Y  Q  R  T  L  C  C  G

 241  GCTCCAAGGGCTTTATGTGTTCCCAGTGCTCCAGGTGCCCCAACCTCTGGATGAGGAACG
  64   S  K  G  F  M  C  S  Q  C  S  R  C  P  N  L  W  M  R  N  G

 301  GGAGCCACTGTTACTACTTCTCAATGGAGAAAAGGGACTGGAACTCTAGTCTGAAGTTCT
  84   S  H  C  Y  Y  F  S  M  E  K  R  D  W  N  S  S  L  K  F  C

 361  GTGCAGACAAAGGCTCGCATCTCCTTACATTTCCGGACAACCAGGGAGTGAACCTGTTCC
 104   A  D  K  G  S  H  L  L  T  F  P  D  N  Q  G  V  N  L  F  Q

 421  AGGAGTATGTGGGCGAGGACTTTTACTGGATTGGCTTGAGGGACATCGATGGCTGGAGGT
 124   E  Y  V  G  E  D  F  Y  W  I  G  L  R  D  I  D  G  W  R  W

 481  GGGAAGATGGCCCAGCTCTCAGCTTAAGCATTCTCTCTAACAGCGTGGTACAGAAGTGTG
 144   E  D  G  P  A  L  S  L  S  I  L  S  N  S  V  V  Q  K  C  G

 541  GCACCATCCACAGGTGTGGCCTCCACGCCTCCAGTTGTGAGGTTGCTTTGCAGTGGATCT
 164   T  I  H  R  C  G  L  H  A  S  S  C  E  V  A  L  Q  W  I  C

 601  GTGAGAAGGTCCTGCCCTGAAGGATTCCACTGTGTCCCAAGCCTCAGATCTGCCACATGT
 184   E  K  V  L  P  *

 661  CTTCAAAAAGAGGGAATGGGCATGGGGAACCTCTGTTCACAAAGGTGTCTTTAGCAAATG
 721  CCAAACCTGTTATGATATGCCATTAGACAGGCGTTAGCATTCCTTCCTGGGAGCTGGCAT
 781  TTTTCAACTGGGCTTTCTCAGTCATGTTAGCCATTTAAAGCCTAAATCTGGGCAAATGAA
 841  ATAGATAAAATTTATTTTGATGGCTCTTACTGCACAAACTCACCCTGGCTTTCTCATCCC
 901  ATACTCTGCCATATCTATCAAAGATATGTGCAAAACTATTCATCTGCAGAAGAACCCCCA
 961  CCACGGTCAATAACACATTACATAGACATCGAATAGAGACAGAAAAGCAAACACCTCCTG
1021  TTCTCACTCCTGCTTGGAAGCTGAAGTAGCTCAAGCCTGAGGTGTAGGGAGAAGTGCAGT
1081  GGTTACCAGAGTCCAGGAGACTGAAGGGATGGTAGAGGTTGGTTAATGGTTTGGCTGGTG
1141  TGGGGTGACCATCATGATTAATGATTGTTGTATGTTTGCCAATATGTTGTGAACTTCCGG
1201  ATAGCGAGGTGGAAGGACCGTGGGTGTTACCAAATGCCTGCAGGAGAGATGTGCTGAGAA
1261  CCCTGACTGGATGATTTCCACACACATTGAAATATCACACTGTGCCCCATAAATGTGTAC
1321  AATCATTATCTATCCCTAATTTCCCTAAAAATTAAAGAAGTCCCAATTAAAATAAAAAAT
1381  ACCTTTCTGCTAAAAAAAAAAAAAAAAAAAAAAAAAAAAAAAAAAAAAAAAAAAAAAAAA
1421  AAAAAAAAAAAAAAAAAAAAA
```

FIG.5

```
   1 CACCCTGCTTACTGTCGTCACTCCCTGCTGAGTGTGAAGGGCGTTGGGTGGAGATGGCCG
   1                                                          M  A  D

  61 ACAACTCTATCTACTCAACATTAGAGCTGCCTGCTGCACCTCGAGTCCAAGATGACTCCA
   4  N  S  I  Y  S  T  L  E  L  P  A  A  P  R  V  Q  D  D  S  R

 121 GATGGAAGGTCAAAGCTGTCTTACACCGACCCTGTGTTTCCTACCTTGTGATGGTGGCTT
  24  W  K  V  K  A  V  L  H  R  P (C) V  S  Y  L  V  M  V  A  L

 181 TGGGGCTTTTGACTGTGATTCTCATGAGTCTACTGTTGTACCAACGGACTCTGTGCTGTG
  44  G  L  L  T  V  I  L  M  S  L  L  Y  Q  R  T  L (C)(C) G

 241 GCTCCAAGGGCTTTATGTGTTCCCAGTGCTCCAGGTGCCCCAACCTCTGGATGAGGAACG
  64  S  K  G  F  M (C) S  Q (C) S  R (C) P  N  L  W  M  R [N  G

 301 GGAGCCACTGTTACTACTTCTCAATGGAGAAAAGGGACTGGAACTCTAGTCTGAAGTTCT
  84  S] H (C) Y  Y  F  S  M  E  K  R  D  W [N  S  S] L  K  F (C)

 361 GTGCAGACAAAGGCTCGCATCTCCTTACATTTCCGGACAACCAGGGAGTGAACCTGTTCC
 104  A  D  K  G  S  H  L  L  T  F  P  D  N  Q  G  V  N  L  F  Q

 421 AGGAGTATGTGGGCGAGGACTTTTACTGGATTGGCTTGAGGGACATCGATGGCTGGAGGT
 124  E  Y  V  G  E  D  F  Y  W  I  G  L  R  D  I  D  G  W  R  W

 481 GGGAAGATGGCCCAGCTCTCAGCTTAAGCATTCTCTCTAACAGCGTGGTACAGAAGTGTG
 144  E  D  G  P  A  L  S  L  S  I  L  S  N  S  V  V  Q  K (C) G

 541 GCACCATCCACAGGTGTGGCCTCCACGCCTCCAGTTGTGAGGTTGCTTTGCAGTGGATCT
 164  T  I  H  R (C) G  L  H  A  S  S (C) E  V  A  L  Q  W  I (C)

 601 GTGAGAAGGTCCTGCCCTGAAGGATTCCACTGTGTCCCAAGCCTCAGATCTGCCACATGT
 184  E  K  V  L  P  *

 661 CTTCAAAAAGAGGGAATGGGCATGGGGAACCTCTGTTCACAAAGGTGTCTTTAGCAAATG
 721 CCAAACCTGTTATGATATGCCATTAGACAGGCGTTAGCATTCCTTCCTGGGAGCTGGCAT
 781 TTTTCAACTGGGCTTTCTCAGTCATGTTAGCCATTTAAAGCCTAAATCTGGGCAAATGAA
 841 ATAGATAAAATTTATTTTGATGGCTCTTACTGCACAAACTCACCCTGGCTTTCTCATCCC
 901 ATACTCTGCCATATCTATCAAAGATATGTGCAAAACTATTCATCTGCAGAAGAACCCCCA
 961 CCACGGTCAATAACACATTACATAGACATCGAATAGAGACAGAAAAGCAAACACCTCCTG
1021 TTCTCACTCCTGCTTGGAAGCTGAAGTAGCTCAAGCCTGAGGTGTAGGGAGAAGTGCAGT
1081 GGTTACCAGAGTCCAGGAGACTGAAGGGATGGTAGAGGTTGGTTAATGGTTTGGCTGGTG
1141 TGGGGTGACCATCATGATTAATGATTGTTGTATGTTTGCCAATATGTTGTGAACTTCCGG
1201 ATAGCGAGGTGGAAGGACCGTGGGTGTTACCAAATGCCTGCAGGAGAGATGTGCTGAGAA
1261 CCCTGACTGGATGATTTCCACACACATTGAAATATCACACTGTGCCCCATAAATGTGTAC
1321 AATCATTATCTATCCCTAATTTCCCTAAAAATTAAAGAAGTCCCAATTAAAATAAAAAAT
1381 ACCTTTCTGCTAAAAAAAAAAAAAAAAAAAAAAAAAAAAAAAAAAAAAAAAAAAAAAAAAA
1421 AAAAAAAAAAAAAAAAAAAA
```

FIG. 6

```
r-MAFA (188)  75 C PNL W MRNGSH C YYFSMEKRD W NSSLKF C ADKGSH L LTFPDNQGVNLFQEYVGEDF..Y
m-Fce2 (331) 186 C PKN W LHFQQK C YYFGKGSKQ W IQARFA C SDLQGR L VSIHSQKEQDFLMQHINKKDS..
h-CD69 (199)  85 C SED W VGYQRK C YFISTVKRS W TSAQNA C SEHGAT L AVIDSEKDMNFLKRYAGREE..H
m-NK11 (227)  94 C PQD W LSHRDK C FHVSQVSNT W EEGLVD C DGKGAT L MLIQDQEELRFLLDSIKEKYNSF
m-LECI (301) 170 C PVN W VEFGGS C YWFSRDGLT W AEADQY C QLENAH L LVINSREEQDFVVKHRSQFHI..

W I GL R.DIDG..WR W ED G PALSLSI.........LSNSV...VQK C GTIHRCGLHA.SS C EV.ALQ W I C EKVLP 188
W I GL QDLNMEGEFV W SD G S..PVGYSNWNPGEPNN.. ..GGQGED C VMMRGSGQWNDAF C RSYLDA W V C EQLAT 310
W V GL K.KEPGHPWK W SN G KEFNNW..........FNVTG...SDK C VFLKNTEVSS.ME C EK.NLY W I C NKPYK 199
W I GL RYTLPDMNWK W IN G STLNSDV.........LKITGDTENDS C AAISGDKVTFE.S C .NSDNR W I C QKELY 215
W I GL TD..RDGSWK W VD G TDYRSNYRNWAFTQPDNWQGHEQGGGED C AEILSDGHWNDNF C QQ.VNR W V C EKRRN 298
```

DNA MOLECULE ENCODING A MAST CELL FUNCTION-ASSOCIATED ANTIGEN (MAFA)

FIELD OF THE INVENTION

The present invention is generally in the field of inflammation and allergy and relates to substances which may be useful in controlling the cellular processes which result in inflammation or allergic reactions. More specifically, the present invention concerns a new isolated DNA molecule encoding a protein, the mast cell function-associated antigen (hereinafter MAFA), which is capable of modulating the response to the type I Fcε receptor for IgE (hereinafter FcεRI), which is present on the surface of mast cells, basophils, eosinophils and Langerhans cells, and which activates these cells. The present invention also concerns recombinant expression vectors containing the MAFA-encoding DNA molecule and host cells transformed by the vectors which are capable of expressing biologically active MAFA. The invention also provides a method for screening potential ligands of MAFA, which ligands alone or in combination with MAFA may be used to prevent inflammation and allergy.

BACKGROUND OF INVENTION AND PRIOR ART

Mast cells and basophils are immunologically activated by aggregation of IgE molecules bound to the FcεRI with multivalent antigen. Cell response can also be induced by directly cross-linking the FcεRI, for example, with anti-receptor antibodies. Clustering of the FcεRI on mast cells and basophils by either IgE and polyvalent antigen or directly by specific monoclonal antibodies, initiates a cascade of biochemical processes coupling to the cells secretory response. These include: (i) the activation of receptor-associated protein tyrosine kinases (Eiseman and Bolen, 1992) and phosphatases (Hampe and Pecht, 1994) causing a transient increase in tyrosine phosphorylation of several cellular proteins (Benhamou et al., 1990 and 1992); (ii) an increase in phosphoinositides hydrolysis (Beaven et al., 1984a) resulting from PLCγ1 activation (Li et al., 1992); and (iii) the rise in the intracellular concentration of free calcium ions (Beaven et al., 1984b). The final response to this stimulus is the secretion of granule-stored mediators and the de novo synthesis and secretion of mediators of inflammation and the allergic response, including histamine, serotonin, arachidonic acid metabolites, like leukotrienes (Ortega et al., 1989), prostaglandins, and several cytokines (Bradding et al., 1993; Galli et al., 1991).

Several mast cell membrane components different from known FcεRI subunits have been identified on the rat mucosal type mast cell line RBL-2H3, mainly by specific monoclonal antibodies (mAb), and shown to modulate the FcεRI-mediated secretory response. G63, a mAb that binds a membranal glycoprotein named MAFA, for mast cell function-associated antigen (Ortega and Pecht, 1988), was shown to inhibit both the FcεRI-induced signalling cascade upstream to PLCγ1 activation (e.g. phosphatidylinositide hydrolysis products and transient rise in the cytoplasmic concentration of free $Ca^{2+}$ ions), and the culminating secretion of the cells' granule contents (Ortega and Pecht, 1988). mAb G63 inhibitory effect required MAFA clustering, and was not due to interference with IgE- FcεRI interactions. Still, cross-linking of FcεRI-IgE complexes by multivalent antigen also led to co-clustering of the MAFA with the aggregated FcεRI and in the enhancement of its internalization (Ortega et al., 1991).

The MAFA has been identified as a glycoprotein with a MW of 28 to 40 kDa distinct from any known FcεRI subunit by immunoprecipitation with mAb G63 and reducing SDS-PAGE. When the SDS-PAGE was run under non-reducing conditions, the observed pattern was different: a component with an apparent MW of 60–82 kDa was detected in addition to the above described 28 to 40 kDa band, suggesting that the MAFA is a disulfide-linked dimer composed of subunits of similar size (Ortega and Pecht, 1988).

Following the discovery of MAFA, the present inventors sought to isolate and sequence the gene encoding this protein. However, the standard procedures for isolating and cloning desired genes proved to be unsuitable for isolating and cloning the gene encoding MAFA (hereinafter mafa). Originally, peptides thought to be derived from MAFA were obtained and sequenced using standard peptide sequencing procedures, and used to prepare oligonucleotides for use as probes to isolate the mafa sequence in RBL cells. However, this proved to be unsuccessful and it was found that the original peptides were not MAFA-derived. Further, as MAFA is not an enzyme and there is no known natural ligand which binds to MAFA, it was also not possible to carry out usual standard cloning and subsequent screening procedures. Thus, after considerable experimental effort, the successful cloning, isolation and sequencing of the mafa sequence, in accordance with the present invention, was achieved by so-called "eukaryotic expression-cloning", a procedure detailed herein below in which from a large number of transfected mammalian cells a single suitable transfected clone was identified and isolated using emulsion autoradiography (Gearing et al., 1989) by virtue of its expressing the MAFA correctly as a surface-bound protein. This isolation was here for the first time achieved by using as ligand a radiolabeled monoclonal antibody (G63) specific for MAFA. Moreover, only upon the successful isolation and sequencing of the mafa sequence, in accordance with the present invention, was it possible to determine precisely the molecular weight of the protein (both the monomeric and homodimeric forms), the glycosylation sites on the protein, and also to perform an accurate sequence determination of the cDNA encoding it and deduce its amino acid sequence, thus allowing a comparative analysis of the MAFA sequence with the sequences of other known mammalian proteins.

There has been a long-felt need to provide a highly-specific modulator of inflammation and/or allergic reactions (i.e. reagents that would block the secretory response of MC and basophils to the immunological stimulus). Most known substances used to treat inflammation and allergic reactions, e.g. anti-histamines, treat the consequences of the secretion process rather than inhibit it. In addition, they also have undesirable side-effects. MAFA is a highly-specific modulator of the initial stages of the cellular processes leading to inflammation and allergic reactions. The characterization of mafa affords a tool for screening for potential MAFA ligands, which ligands alone or in combination with MAFA can be used to prevent inflammatory and allergic reactions. The DNA molecule encoding MAFA provides a basis for large-scale production of this potentially pharmaceutically-important protein, in its native form or in a modified soluble form thereof.

SUMMARY OF THE INVENTION

Naturally-occurring MAFA is membrane-anchored and thus the isolation, in accordance with the present invention, of the DNA molecule encoding MAFA provides a means for obtaining one or more soluble form(s) of MAFA, which may be used to screen for potential ligands, e.g. saccharides, lipopolysaccharides, proteins, glycoproteins, and glycopeptides that bind specifically to MAFA. Moreover, preparation of such soluble form(s) of MAFA also provides a means for generating additional monoclonal antibodies having specificity for different epitopes (from that of mAb G63) of MAFA.

Thus, the present invention provides an isolated DNA sequence encoding a mammalian mast cell function-associated antigen (MAFA). Further, the present invention also provides an isolated DNA sequence encoding a polypeptide product of prokaryotic or eukaryotic host expression, said product having all or part of the primary structural conformation of a mammalian MAFA and preferably having the binding specificity of MAFA as determined in a binding assay with an anti-MAFA monoclonal antibody (mAb), for example, mAb G63 (G63).

In one embodiment, the present invention comprises a DNA sequence selected from the group consisting of:

(a) DNA molecules comprising a nucleotide sequence encoding native mammalian MAFA;

(b) DNA molecules having a nucleotide sequence derived from the coding region of a native mammalian MAFA gene (mafa) which encode a soluble form of MAFA;

(c) DNA molecules capable of hybridization to the DNA molecules of (a) and (b) under moderately stringent conditions and which encode a soluble form of MAFA;

(d) DNA molecules which are degenerate, as a result of the genetic code, to the DNA sequences of (a), (b) and (c), and which encode a soluble form of MAFA; and (e) DNA molecules according to (b), (c) or (d) which encode a form of soluble MAFA that has the binding specificity of native MAFA, as determined in a binding assay with a monoclonal antibody to native MAFA.

In other embodiments, the invention provides the cDNA sequence depicted in FIG. 5 (SEQ ID NO:4) which encodes native MAFA and cDNA sequences which encode a soluble form of MAFA (SEQ ID NO:5) having said binding specificity of MAFA and an amino acid sequence which is contained within the sequence of amino acid residues 1–188 depicted in FIG. 5 (SEQ ID NO:5).

The present invention also provides recombinant expression vectors comprising any of the above noted DNA sequences of the invention; prokaryotic or eukaryotic host cells transfected by the vectors and capable of expressing native MAFA or a soluble form of MAFA having said binding specificity of MAFA; a process for preparing MAFA or said soluble form thereof comprising culturing suitable host cells under conditions promoting expression; and a mammalian MAFA and soluble forms thereof produced by the process.

As another aspect, the present invention provides a method for screening potential ligands of MAFA which comprises:

(i) providing a soluble form of MAFA;

(ii) attaching said soluble form of MAFA to a suitable matrix; and (iii) monitoring ligand binding to the matrix-bound soluble MAFA of (ii) by bringing a potential ligand, selected from saccharides, lipopolysaccharides, proteins, glycoproteins, and glycopeptides, into contact with said matrix-bound soluble MAFA and purifying the complex composed of MAFA and MAFA-ligand and eluting the isolated MAFA-ligand for the analysis of its chemical nature by standard biochemical procedures.

To provide a soluble form of MAFA for use in the above screening method of the invention, it is possible by way of the usual standard methods, to prepare such a MAFA, by for example, inserting a DNA molecule of the invention having the mafa sequence depicted in FIG. 5 into a suitable vector; modifying said mafa sequence by addition, deletion or substitution mutagenesis of more than one codon to generate a modified-MAFA-encoding vector; expressing said modified-MAFA-encoding vector in a suitable host cell to obtain a modified-MAFA protein that is a soluble form of MAFA, or converting said modified-MAFA into a soluble form of MAFA if necessary; assaying the binding specificity of said soluble MAFA by determining its ability to bind to a monoclonal antibody (mAb) specific to MAFA; and selecting a soluble form of MAFA capable of binding said mAb. The mafa sequence can be mutagenized using standard methods (Sambrook et al., 1989) to delete or change the amino-terminal non-cleavable signal sequence in order to produce a secreted, soluble MAFA. Alternatively, soluble MAFA can be obtained using commercially available systems for inserting all or part of the mafa sequence into an appropriate vector able to direct its expression as part of a fusion protein (containing a tag for affinity purification) in the host of choice (prokaryotic, insect cells or mammalian cell lines).

Accordingly, the present invention also provides ligands specific to MAFA obtained by the above screening method of the invention, and compositions containing one or more of said ligands alone or in combination with the MAFA which may be used to prevent inflammatory and allergic reactions.

BRIEF DESCRIPTION OF THE DRAWINGS

FIG. 5 depicts the nucleotide sequence (SEQ ID NO:4) of the cloned MAFA cDNA. The deduced amino acid sequence (SEQ ID NO:5) of the MAFA is shown in the one-letter code. Bases and residues are numbered on the left. The predicted transmembrane domain is underlined, the putative N-glycosylation sites are boxed and the cysteines are circled. The TGA stop codon is marked with an asterisk and the polyadenylation signal is overlined.

FIG. 6 shows sequence homology between the MAFA and members of the C-type lectin family. The MAFA carboxy terminal 114 amino acids (SEQ ID NO:6) are aligned with the carbohydrate recognition region (CRD) of selected C-type lectins with which the highest degree of homology is shared. Fully conserved residues are boxed and the motifs Cys-Tyr-Tyr-Phe (residues 12–15 of SEQ ID NO:6) and Trp-Ile-Gly-Leu (residues 58–61 of SEQ ID NO:6) are shadowed. The first and last amino acid of each displayed sequence is numbered in bold and the total length of the respective polypeptide is given in brackets. m-LECI: mouse asialoglycoprotein receptor 2 (SEQ ID NO:10); m-Fce2: mouse FcεRII (SEQ ID NO:7) ; h-CD69: human CD69(SEQ ID NO:8); m-NK11: mouse natural killer cell antigen NKR-P1 (SEQ ID NO:9). The sequences were aligned with the PILEUP program in the GCG sequence analysis software. The nucleotide sequence of the cloned MAFA cDNA will appear in the EMBL, DDBJ, and GenBank Nucleotide Sequence Databases under the accession number X79812.

DETAILED DESCRIPTION OF THE INVENTION

Figure 1:
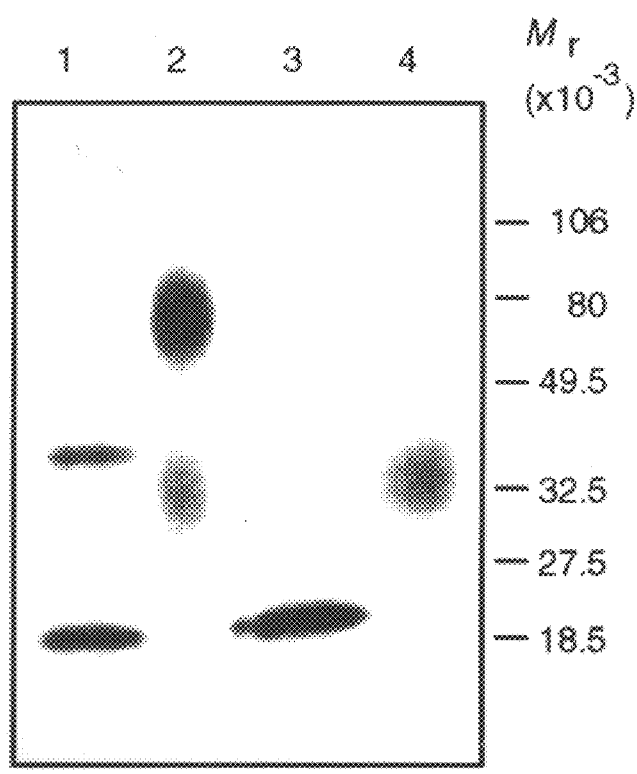
FIG. 1 depicts electrophoretic analysis of the native and N-deglycosylated MAFA. A lysate derived from $10^8$ surface-radioiodinated RBL-2H3 cells was incubated with mAb G63-coated beads, which were then washed and incubated with N-glycosidase F (lanes 1 and 3) or with buffer alone (lanes 2 and 4), as described in Experimental Procedures. The immuno-precipitates were eluted by boiling in SDS-PAGE sample buffer and analyzed on a 10 to 17.5%. polyacrylamide gel under reducing (lanes 3 and 4) or non-reducing conditions (lanes 1 and 2). The gel was then dried and autoradiographed.

The present invention concerns a DNA sequence encoding MAFA, a modulator of the type I FcεRI-mediated activation of mast cells and basophils. A eukaryotic cDNA expression library was constructed in pcDNA I (InVitrogen), the cDNA being derived from the poly A+m RNA of the RBL-2H3 cell line, from which there was isolated and subsequently sequenced the cDNA molecule which encodes MAFA (the mafa cDNA). Comparison of the deduced amino acid sequence with known proteins, has shown that MAFA is a type II integral membrane glycoprotein that is in fact, a new member of the superfamily of C-type animal lectins.

Naturally-occurring MAFA is a membrane-bound protein and it is not soluble. As noted above, one of the aspects of the present invention is a method to screen for potential ligands which bind specifically to MAFA, and which ligands alone, in a mixture, or in combination with MAFA may be useful to prevent inflammation and allergy. For the purpose of screening potential ligands it is, however, necessary to first provide a soluble form of MAFA, preferably one which has retained the binding specificity of MAFA as determined by an assay with monoclonal antibodies to MAFA, e.g. mAb G63. Moreover, obtention of a soluble form of MAFA also enables the generation of additional mAbs specific for MAFA which bind epitopes of MAFA different from those of mAb G63, and which may be useful, for example, for use in the above screening procedure, i.e. they can be used in a competitive binding assay with potential ligands to determine the binding specificity and affinity of such ligands to MAFA.

Preparation of the cloned cDNA sequence encoding MAFA, according to the present invention, provides the means for obtaining a soluble form of MAFA. To prepare a soluble form of MAFA, the usual standard techniques of recombinant DNA technology may be employed (see, for example, Sambrook et al., 1989). For example, the cloned cDNA encoding the mafa sequence depicted in FIG. 5 (SEQ ID NO:4), can be manipulated by addition, deletion or substitution mutagenesis procedures using standard methods (Sambrook et al., 1989) to generate a series of modified MAFA-encoding sequences and recombinant vectors containing them, which when expressed in a suitable host, will provide a series of MAFA derivatives, differing from one another and from the native MAFA by having more than one amino acid residues added, deleted or substituted with another amino acid residue. These MAFA derivatives may then be analyzed by standard procedures to ascertain whether or not they are soluble. Should there arise a situation where suitable soluble MAFA derivatives are not obtained, then it is also possible to convert, by known methods, either the native MAFA or non-soluble MAFA derivatives into soluble forms.

As it is known that for many membrane-bound proteins it is possible to specifically prepare and isolate their extracellular domains, which represent the soluble forms of these proteins and retain the binding specificity of these proteins for their ligands, MAFA may therefore also be manipulated to obtain the soluble extracellular domain of MAFA (residues 55–188 of SEQ ID NO:5), this being a soluble derivative of MAFA. In order to prepare such a soluble derivative of MAFA, it is possible, for example, to insert, in a recombinant vector encoding the native mafa sequence, a target sequence that is cleavable by specific proteases, e.g., the blood coagulation factor Xa (the tetrapeptide sequence Ile-Glu-Gly-Arg (SEQ ID NO:11), (Nagai and Thogersen, 1987) into the extracellular domain of MAFA close to the transmembranal stretch of MAFA. The subsequent expression of such a recombinant vector encoding the so-modified mafa sequence by the appropriate host cells, transfected with this vector, such as, for example, prokaryotic, insect or mammalian cells, will enable the production of the extracellular domain of MAFA, i.e. a soluble form of MAFA, once these cells are treated with the respective protease, e.g. factor Xa. The above transfected cells would express MAFA as a membrane-bound protein and when treated with the protease, the extracellular portion of MAFA will be cleaved at the target sequence site resulting in the release of this extracellular portion of MAFA into the culture medium from which it may be collected and purified.

Another possibility for preparing such a soluble, extracellular domain of MAFA is by deleting, in a recombinant vector encoding the mafa sequence, the cytoplasmic (or intracellular) domain and the transmembrane stretch of MAFA and fusing the remaining extracellular domain to a leader sequence directing the secretion of this fusion protein. This leader sequence may be, for example, the hydrophobic leader sequence of the glycoprotein D (gD-1) from herpes simplex virus type I (HSVI) (Caras et al., 1987). The expression of such a modified MAFA sequence by the appropriate transfected cells (see above) yields a fusion protein, being essentially the extracellular domain of MAFA, i.e. a soluble form of MAFA, that is constitutively secreted (for constitutive secretion of such fusion proteins, see Caras et al., 1987) into the culture medium from which it may be collected and purified.

The above noted manipulation and subsequent expression of the mafa sequence in the host cells are carried out by standard procedures (Sambrook et al., 1989).

The cDNA encoding native MAFA or any of the above mentioned modified MAFA-encoding sequences can be expressed in eukaryotic or prokaryotic host cells that are transformed by a vector containing the mafa cDNA or modified (deletion or substitution) mafa cDNA. Eukaryotic host cells are preferable in view of the fact that MAFA is a homodimeric glycoprotein, and correct post-translational processing, e.g. dimerization and glycosylation take place only in eukaryotic host cells. Further, it may also be preferable to prepare the MAFA derivatives, some of which may be soluble, in eukaryotic host cells so that these too have the correct post-translational processing. However, prokaryotic expression of MAFA is useful for the production of large amounts of MAFA and MAFA derivatives.

Suitable eukaryotic host cells may be any of the well known yeast, insect or mammalian cell lines. The monkey COS-7 cell line was found to be suitable for experimental MAFA expression in accordance with the present invention. For large scale commercial production other suitable cells, such as CHO and insect cells, may be used.

For the purification of the above mentioned soluble MAFA derivatives, for example, the extracellular domain of MAFA, the standard procedures of affinity chromatography may be employed by using a suitable, known solid support or matrix to which is coupled a MAFA-specific monoclonal antibody, e.g. mAb G63.

The purified soluble derivatives of MAFA, e.g. the extracellular domain of MAFA, may be coupled to a solid support or matrix for use in screening for ligands that are specific to MAFA. Potential MAFA-ligands, e.g. simple or complex saccharides, proteins, glycoproteins, lipopolysaccharides or glycolipids will be brought into contact with such a MAFA-coupled solid support, and subsequently the ligand(s) which bind to MAFA may be specifically eluted, purified and their chemical nature analyzed, all by way of standard biochemical procedures. In this way, it will be possible to identify the naturally-occurring MAFA-specific ligands as well as any other MAFA-specific ligands, e.g. synthetically produced sugars.

For the preparation of a soluble MAFA derivative and its use in screening for potential ligands which are capable of binding specifically to MAFA, a number of methods may be employed, as noted above. An example of one procedure for preparing a soluble MAFA derivative and its subsequent use to screen for MAFA-specific ligands is as follows:

(i) inserting all or part of the mafa sequence depicted in FIG. 5 in an appropriate commercially available vector able to direct the expression of the MAFA as a soluble protein in the form of a tagged fusion protein;

(ii) expressing the above mentioned modified mafa sequence in a suitable host cell (prokaryotic, insect cell or mammalian cell line) and purifying the expressed MAFA-fusion protein with an affinity chromatography column containing a ligand for the tag present in the fusion protein, thus obtaining a soluble MAFA derivative;

(iii) assaying the binding specificity of the soluble MAFA derivative by using a monoclonal antibody specific to MAFA, e.g. mAb G63, and selecting those MAFA derivatives which bind to said antibody, these being soluble derivatives of MAFA that have retained the binding specificity of MAFA as determined in a binding assay with mAb G63;

(iv) attaching, if necessary, the selected soluble derivative (s) of MAFA to a suitable, known, solid support or matrix;

(v) bringing potential ligands, e.g. saccharides, proteins, lipopolysaccharides, glycoproteins, and glycopeptides, into contact with the soluble MAFA derivative or soluble MAFA derivative bound to the solid support or matrix; and (vi) purifying the complex composed of MAFA and MAFA-ligand and eluting the isolated MAFA-ligand for the analysis of its chemical nature by standard biochemical procedures.

The invention will now be described in more detail in the following non-limiting examples and the accompanying drawings

EXAMPLES

Experimental Procedures (a) Cell Lines and Tissue Culture

RBL-2H3 cells were obtained from Dr. R. P. Siraganian, HIH, Bethesda, Md. (Barsumian et al., 1981). They were maintained in Eagle's minimal essential medium with Earle's salts (MEM, GIBCO, Grand Island, N.Y., USA) supplemented with 10% FCS (GIBCO), 2 mM glutamine, and antibiotics (penicillin-streptomycin mixture, Bio-Lab, Jerusalem, Israel). The G63 hybridoma cells (Ortega and Pecht, 1988) were maintained in DMEM supplemented with 10% FCS, 2 mM glutamine, 2 mM sodium pyruvate (Bio-Lab), and antibiotics. KU812 cells (kindly provided by Dr. E. Razin, Hebrew University of Jerusalem) and COS-7 cells were maintained in DMEM, supplemented with 10% FCS and antibiotics. P815 cells (obtained from Dr. R. Levi, The Weizmann Institute of Science) were maintained in RPMI 1640 (GIBCO), supplemented with 10% FCS, 25 mM HEPES, 2 mM glutamine and antibiotics. All cells were incubated in a humidified atmosphere with 7% $CO_2$ at 37° C.

(b) Purification of mAb G63 mAb G63 (IgG1) was purified from G63 hybridoma culture supernatants by chromatography on protein A-Sepharose (Pharmacia, Uppsala, Sweden). The mAb was eluted with 0.2 M sodium citrate (pH 4.5) directly into tubes containing neutralizing 2 M Tris buffer (pH 8.2). The mAb was dialyzed against 0.1 M HEPES pH 8.0, and stored at −20° C.

(c) Iodination of mAb G63

The chloramine-T method was used for labeling with [$^{125}$I]-sodium iodide (Amersham, UK). The specific activity obtained was typically 6700 cpm/fmol.

(d) Radioiodination of Cell Membrane Components and Cell Lysis

RBL-2H3 and COS-7 cells were surface iodinated by the lactoperoxidase technique (Marchalonis, 1966). To $10^7$ cells washed three times with PBS, 1 mCi of [$^{125}$I]-sodium iodide was added. At 0, 4, 8, 12, and 16 min, 45 $\mu$l of a 0.5 mg/ml solution of lactoperoxidase (Sigma, St. Louis, Mo., USA) and 10 $\mu$l of 0.03% $H_2O_2$ were added. Four minutes after the last addition, cells were washed four times with PBS. The cells were solubilized by 0.5% Triton X-100 in 10 mM HEPES, 10% glycerol, 0.15 M NaCl (pH 7.6) in the presence of 2mM phenylmethyl-sulfonyl fluoride, 1 $\mu$g/ml pepstatin, 2 $\mu$g/ml leupeptin, and 10 mM iodoacetamide in a final volume of 1.5 ml. After 15 min on ice, non-solubilized material was removed by centrifugation at 20,000×g for 10 min at 4° C.

(e) Immunoprecipitation and Deglycosylation mAb G63 was coupled to Affigel-10 (Bio-Rad, Richmond, Calif., USA), as recommended by the manufacturer, at a ratio of 10 mg of antibody per ml of Affigel-10. 10–50 $\mu$l of mAb G63-coated beads were added to the cell lysates and the suspensions were gently rocked at 4° C. for 4 hours. The beads were then washed three times batchwise with a buffer containing 0.05% Triton X-100 in 10 mM HEPES, 10% glycerol and 0.5 M NaCl (pH 7.6). Finally, the beads were either resuspended in deglycosylation buffer (see below) or boiled in SDS-PAGE sample buffer (9% SDS, 30% glycerol, 0.02% bromophenol blue, 185 mM Tris-Cl pH 6.8) for elution and electrophoresis of the bound MAFA. For cleavage of the N-linked oligosaccharide side chains, the G63-coated beads carrying the immunoadsorbed-MAFA were resuspended in 50 $\mu$l Tris-Cl 10 mM pH 7.0 containing 0.1% SDS and 0.5% β-mercaptoethanol, and boiled for 5 min. After cooling to room temperature, 1% Triton X-100, 1 mM EDTA, 2 mM PMSF, and 4 units/ml N-glycosidase F (Boehringer Mannheim) were added followed by incubation at 37° C. for 18 hours with continuous gentle shaking. Then, the supernatant was separated by centrifugation, and the beads were boiled for 3 min in SDS-PAGE sample buffer. The buffer was then combined with the recovered supernatant, further incubated at 100° C. for 3 min and analyzed by SDS-PAGE. Discontinuous SDS-PAGE was performed using the acrylamide concentrations indicated in each case.

(f) Tryptic Peptide Mapping of the Monomeric and Dimeric Forms of the MAFA

Peptide mapping of the MAFA monomer and dimer was performed as described elsewhere (Elder et al., 1977). Both forms of previously deglycosylated MAFA were localized on a polyacrylamide gel after non-reducing SDS-PAGE by autoradiography. The corresponding gel slices were then cut out and submitted to further iodination in the presence of chloramine T. The gel pieces were then washed with several changes of 10% methanol, dried and rehydrated in 500 $\mu$l of 50 $\mu$g/ml trypsin (Sigma) in 50 mM $NH_4HCO_3$ buffer (pH 8.0). The samples were incubated at 37° C. for 12 hours with gentle agitation, after which the supernatants were removed, lyophilized, and analyzed on cellulose-coated plates (10×10 cm; Merck, Darmstadt, Germany) by sequential high voltage electrophoresis and chromatography (Elder et al., 1977). Finally, the plates were dried and autoradiographed.

(g) Endoproteinase Lys-C Digestion of Deglycosylated MAFA

The MAFA was digested with endoproteinase Lys-C (Boehringer Mannheim) essentially as described elsewhere (Fernandez et al., 1992). Basically, G63 immunoprecipitates of surface-labeled RBL-2H3 cell lysates were deglycosylated and submitted to reducing SDS-PAGE, after which wet electrophoretic transfer to nitrocellulose was performed in a buffer containing 25 mM Tris, 190 mM glycine and 10% methanol. The bands of interest were then visualized by autoradiography and the corresponding nitrocellulose strips were excised and incubated with 0.5 units of endoproteinase Lys-C at 37° C. for 24 hours in a volume of 50 $\mu$l. Following digestion, the peptides were eluted by sonication in 0.1% TFA and concentrated in a Speed Vac (Savant Instruments, Farmingdale, N.Y., USA) to a final volume of 50 ($\mu$1 Finally, the peptides were analyzed by SDS-tricine-PAGE using a 16.5% T-6% C separating gel (Schagger and von Jagow, 1987). The gel was dried and autoradiographed.

(h) RBL-2H3 CDN Library Construction

20 $\mu$l polyadenylylated RNA was prepared from RBL-2H3 cells essentially as described (Lin et al., 1991). Homogenates derived from $10^9$ RBL-2H3 cells by the proteinase K/SDS method (Gonda et al., 1982) were stirred for 2 hours at room temperature with approximately 0.1 of oligo dT-cellulose (Boehringer Mannheim) preswollen in high salt buffer containing 0.5 M NaCl, 0.1% SDS, 1 mM EDTA and 10 mM Tris-Cl pH 7.5. The oligo dT-cellulose was collected by centrifugation and washed twice with high salt buffer containing LiCl instead of NaCl, and twice again with the high salt buffer described above. At this point, the oligo dT-cellulose was poured in a sterile disposable column and the poly A+ mRNA was eluted stepwise with low salt buffer containing 0.05% SDS, 1 mM EDTA and 10 mM Tris-Cl pH 7. 5.3 $\mu$g of poly A+ mRNA were converted to double-stranded cDNA as described (Gubler and Hoffman, 1983). Size-fractionated cDNA larger than 0.7 kb in size were pooled, ligated into the plasmid pcDNAI (InVitrogen, San Diego, Calif., USA), and electroporated into MC1061/P3 *Escherichia coli* (Lin et al., 1991). Batches of approximately 10,000 colonies of transformed bacteria were prepared and one tenth of each was frozen in liquid nitrogen and stored at −80° C. Then, plasmid DNA was isolated from the remaining of each pool using P100 columns (Qiagen, Chatsworth, Calif., USA) following the detailed manufacturer's protocol. The recovered plasmid DNA (typically 75–100 μg) was stored at −20° C. till used for transfection of COS-7 cells.

(i) Expression Cloning of the MAFA cDNA

To screen the plasmid pools for those containing MAFA-encoding sequences, COS-7 cells grown on Flaskette glass slide chambers (Nunc, Naperville, Ill., USA), were separately transfected with 3 μg of each plasmid pool using the DEAE-dextran/chloroquine method essentially as described elsewhere (Seed and Aruffo, 1987). The ligand binding assay on the transfected monolayers was performed by replacing the growth medium with 1.5 ml fresh medium containing the radioiodinated mAb G63 (6700 cpm/fmol, 1nM). The Flaskettes were then placed on an orbital shaker at slow motion for 2 hours at room temperature after which the cells were extensively washed by 6 changes of ice-cold PBS. Autoradiographic analysis of transfected cells was performed essentially as described (Gearing et al., 1989). The positive bacterial pool (i.e. the one yielding plasmid DNA capable of driving the expression of the MAFA in transfected COS-7 cells and hence binding the radioactive mAb G63) was then subdivided into smaller pools. The procedure was repeated till the isolation of one single positive clone.

(j) DNA Sequence Analysis

DNA sequencing was performed using the Taq Polymerase-Dye Deoxynucleotide reaction kit (Applied Biosystems) and an Applied Biosystems 373A sequencer and software. Overlapping sequences from both strands were determined and the compilation of the sequence information from individual reactions was done using the Inherit application program and SeqEd sequence editor (Applied Biosystems). Sequence analysis was performed using the University of Wisconsin Genetics Computer Group software package (Version 7.2).

(k) Reverse Transcription-PCR Analysis

Total RNA was purified from the indicated rat organs and RBL-2H3 cells with an RNazol kit (Cinna/Biotecx Laboratories, Friendswood, Tex.). cDNA synthesis and PCR amplification were performed basically as described (Pinkas-Kramarski et al., 1994). The MAFA primers used were oligonucleotides 8077 (5' GCCACTGTTACTACT-TCT 3') and (SEQ ID NO:1) 8075 (5' GACCTTCTCACA-GATCCA 3') (SEQ ID NO:2). The primers for rat β-actin were as described (Jin et al., 1993). Briefly, the first strand of cDNA was synthesized at 37° C. in a reaction mixture that contained reverse transcriptase (5 units, Promega), both MAFA and β-actin antisense oligonucleotides (10 pmol Peach) and RNA (2 μg). One quarter of the reaction mixture as used as template for each of two parallel PCR reactions; [4]iS one of them containing 10 pmol of both β-actin primers, and the other 10 pmol of both MAFA primers. The cycling conditions were set as described (Pinkas-Kramarski et al., 1994). The products (one tenth of the reaction mixture) were resolved by electrophoresis through a 1.2% agarose gel. The MAFA PCR amplification products were capillary transferred to a nylon membrane and probed using an end-labeled internal oligonucleotide (#7596; 5' GGAGTATGTGGGC-GAGG 3') (SEQ ID NO:3) at 42° C. in the presence of 20% formamide. The blot was washed at 42° C. with 0.2× standard saline citrate (SSC) and 0.20% sodium dodecyl sulfate, and autoradiographed.

(l) Metabolic Labeling with 32P and Phosphoanino Acid Analysis $5\times10^6$ RBL-2H3 cells were plated per 100 mm tissue culture dish and cultured for 24 hours. The monolayers were then washed twice with phosphate-free DMEM and starved by a 3 hours incubation in phosphate-free DMEM supplemented with 2% fetal calf serum (previously dialyzed against deionized water) and 50 mM HEPES pH 7.4 (phosphate-free medium). The cells were washed again and then further incubated for 3 hours with 3.5 ml phosphate-free medium supplemented with 750 μCi $^{32}$P-orthophosphate (Rotem Industries, Beer-Sheva, Israel). Samples scheduled for antigenic stimulation were primed by the addition of 10 nM DNP-specific, IgE class mAb (SPE-49) simultaneously with the orthophosphate, and stimulated after the 3 hours long phosphate-incorporation period by the addition of 100 ng/ml DNP11-BSA for two minutes. When indicated, 10 nM mAb G63 was added to the cells 10 minutes prior to lysis or antigen stimulation. The above treatments were stopped by two fast washings with ice-cold PBS and the immediate addition of 1 ml of the above described lysis buffer supplemented with 100 mM NaF, 2 mM sodium orthovanadate and 10 mM sodium pyrophosphate. The cell lysates were scraped with a rubber policeman and transferred to 1.5 ml test tubes. Cell debris were sedimented by centrifugation (1 minute at 15000 rpm in a Beckman microfuge) and the clear supernatants were incubated with a combination of 20 μl of mAb G63-coated agarose beads and 4 μl of protein A-Affigel (Bio Rad) for 3 hours at 4° C. with gentle rocking. After sedimenting, the immunobeads samples were washed as described above and further incubated with N-glycosidase F for 16 hours. After boiling the samples for three minutes in reducing SDS-PAGE sample buffer, the eluates were subjected to electrophoresis through a 15% polyacrylamide gel. The proteins were then electrotransferred to a polyvinylidene difluoride (PVDF) membrane and visualized by autoradiography. The MAFA (20 kDa)-containing PVDF stripes were excised and washed once in methanol and twice in deionized water in siliconized 1.5 ml test tubes. The strips were then heated to 110° C. in 200 μl 6 N HCl for 1 hour. The supernatants were then transferred to fresh test tubes and dried by evaporation. 200 μl deionized water were added, and the samples were dried again. The hydrolysates were then dissolved in 5 μl pH 3.5 buffer (glacial acetic acid:pyridine:water, 5:0.5:94.5, v/v/v) containing 1 μg phosphoserine, phosphothreonine and phosphotyrosine. The phosphoamino acids were separated by electrophoresis on cellulose coated glass plates (Merck) in pH 3.5 buffer at 1 kV for 25 minutes. The plates were then air-dried and the phosphoamino acid standards were visualized upon spraying with 0.2% (w/v) ninhydrin in ethanol. The radioactive phosphoamino acids were then detected by autoradio-graphy and quantified by densitometric analysis.

EXAMPLE 1

The Mr of the MMA Polypeptide Core is 20 kDa

Two highly glycosylated species are immunoprecipitated by the mAb G63 from surface-radioiodinated RBL-2H3 cells. As reported earlier, these were resolved by non-reducing SDS-PAGE as two broad bands (first ranging from 28 to 40 kDa, and the second from 60 to 82 kDa) (FIG. 1 lane 2). Under reducing conditions, only a single broad band, with the lower Mr form was observed (FIG. 1 lane 4). In order to assess the content of N-linked oligosaccharide side chains of the MAFA, a mAb G63-coated beads-immunoprecipitate obtained as before from surface-iodinated cells was incubated in the presence of N-glycosidase F to remove asparagine-linked oligosaccharide side chains, eluted by boiling in SDS-PAGE sample buffer, and analyzed by SDS-PAGE. Under non-reducing conditions, two considerably narrow bands, of Mr 18 and 40 kDa, respectively, were resolved (FIG. 1 lane 1). Hence, the N-linked oligosaccharide side chains account for up to half of the apparent molecular mass of the MAFA. The approximate 1:2 apparent mass ratio of the two deglycosylated species suggested that the heavier one is a homodimer. Under reducing conditions, only the low Mr form of the MAFA could be observed, albeit with a slightly slower mobility, corresponding to an apparent Mr of 20 kDa (FIG. 1 lane 3). The mobility difference is most probably due to the reduction of intramolecular disulfide bonds.

EXAMPLE 2

Subunit Composition of the MAFA

Figure 2:
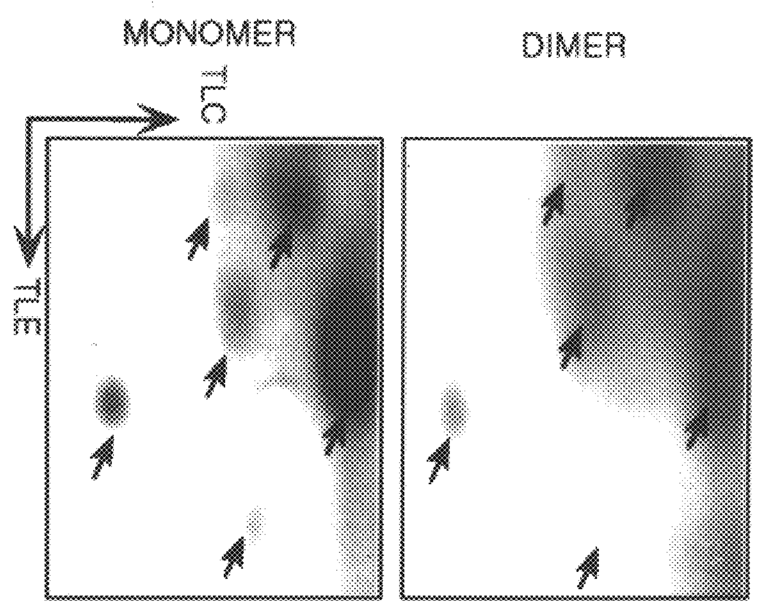
FIG. 2 shows two dimensional tryptic peptide mapping of the monomeric and dimeric forms of N-deglycosylated MAFA. The 18 and 40 kDa forms were separated by SDS-PAGE as described for FIG. 1, visualized by autoradiography, and excised. The two gel pieces were then submitted in parallel reactions to radioiodination with the chloramine T method and to tryptic proteolysis as described in Experimental Procedures. The peptide fragments that eluted from the gel pieces were separated on cellulose-coated plates by electrophoresis in one dimension and chromatography in the other. The plates were then autoradiographed.

In order to examine whether the surface expressed MAFA is indeed assembled in vivo; as a homodimer and exclude the possibility that the higher Mr species is a heterodimer with a subunit that does not undergo cell surface iodination, peptide maps were prepared from tryptic proteolysis fragments derived from both N-deglycosylated 18 and 40 kDa forms of the MAFA. These were first visualized by autoradiography and the correspondent radioactive bands were excised from the polyacrylamide gel. The protein contained in these gel pieces was then further radioiodinated with the chloramine T method. Following proteolysis with trypsin, the peptides that were eluted out of the gel pieces were loaded on cellulose-coated glass plates and separated in the first dimension by electrophoresis and by chromatography in the second (FIG. 2). The marked similarity of the peptide maps derived from both forms of the MAFA indicated that the 40 kDa species is indeed a dimer composed of two identical subunits. Taken together, these results suggest that the MAFA is isolated from PBL-2H3 cell lysates both as a monomer and as a disulfide linked homodimer.

EXAMPLE 3

Cloning and Expression of the MAFA cDNA

Figure 3A:
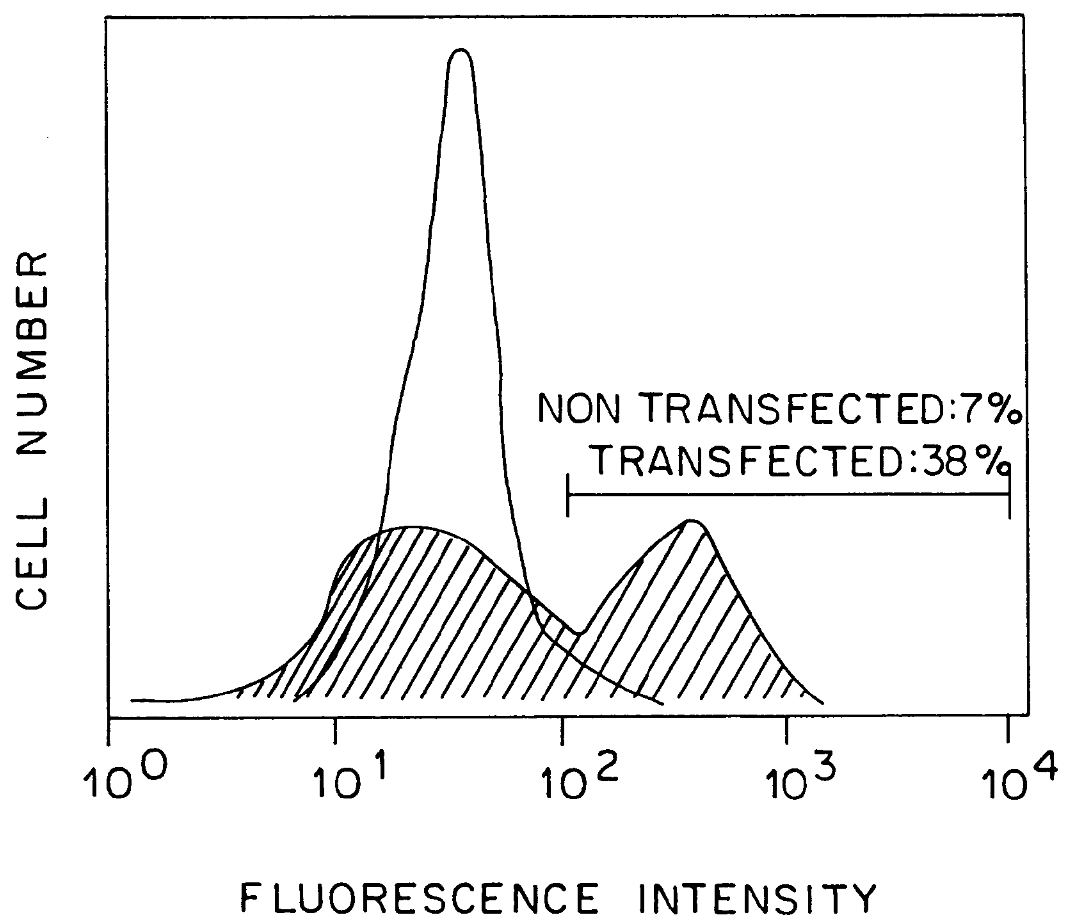
FIG. 3A depicts flow cytometric analysis of COS-7 cells transfected-with the MAFA cloned cDNA, and stained with mAb G63. $10^6$ transfected COS-7 cells were incubated for 30 minutes at room temperature in the presence (shadowed histogram) or absence (empty histogram) of 0.5 mg/ml biotinylated mAb G63, washed, and further incubated for another 30 minutes at 37° C. in the presence of 25 $\mu$g/ml phycoerythrin-labeled streptavidin. The fluorescence associated with 5000 cells of each sample was analyzed with a Becton Dickinson FacScan flow cytometer, and the derived histograms are shown overlaid. The percentage of events under the segment is indicated for each histogram.
Figure 3B:
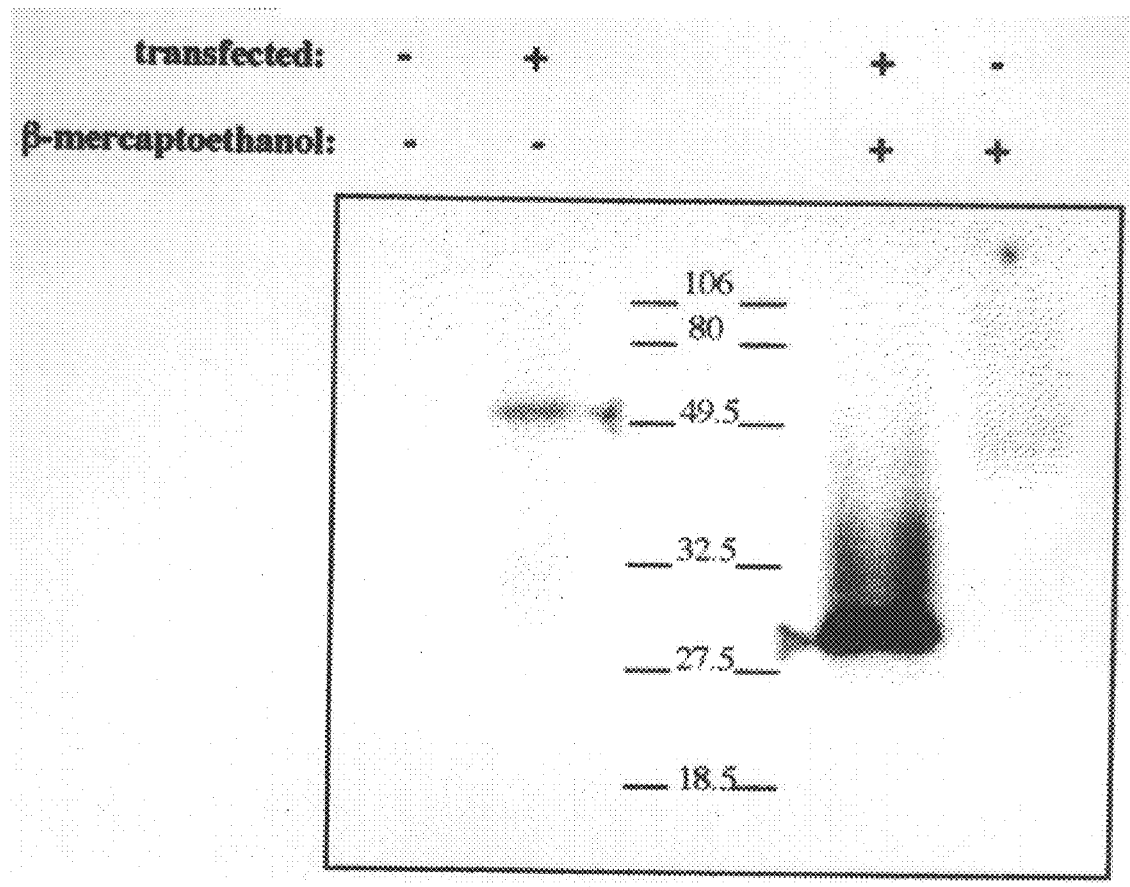
FIG. 3B shows immunoprecipitation and SDS-PAGE analysis of the protein encoded by the cloned cDNA. $10^7$ COS-7 cells, untransfected or transfected with the MAFA cloned cDNA, were surface-radioiodinated, and the derived lysates were incubated with mAb G63-coated beads. The immunoprecipitates were eluted by boiling in SDS-PAGE sample buffer and separated on a 12.5%. polyacrylamide gel under reducing or non-reducing conditions. The gel was then dried and autoradiographed.

A cDNA eukaryotic expression library was constructed using polyadenylylated mRNA isolated from RBL-2H3 cells, which constitutively express the MAFA glycoprotein. 65 pools of 10,000 cDNA clones each were transfected into COS-7 cells on glass-bottom chambers and the monolayers were screened for $^{125}$I-labeled mAb G63-binding cells, performing emulsion autoradiography followed by darkfield microscopy, as described in Experimental Procedures. One of-the 65 cDNA pools (designated with the letter code AO) conferred on the transfected COS-7 cells the ability to bind the radioiodinated mAb G63. The binding specificity was established by its complete inhibition in the presence of a 100 fold excess of unlabeled mAb. Further, it was also unaffected by the addition of a similar excess of an isotype-matched IgG1 antibody (J17; (Ortega et al., 1988)). Sub-pooling of AO, and of the positive pools derived thereof, led to the isolation of a positive clone. The expression of the cloned cDNA by transfected COS-7 cells was analyzed by flow cytometry following sequential incubation with biotinylated mAb G63 and phycoerythrin- labeled streptavidin. 38% of the COS-7 cells used for transfection were stained with mAb G63 (FIG. 3 A), in accordance with the independently determined transfection efficiency of the DEAE-dextran method used (typically 10–50%).

Figure 4A:
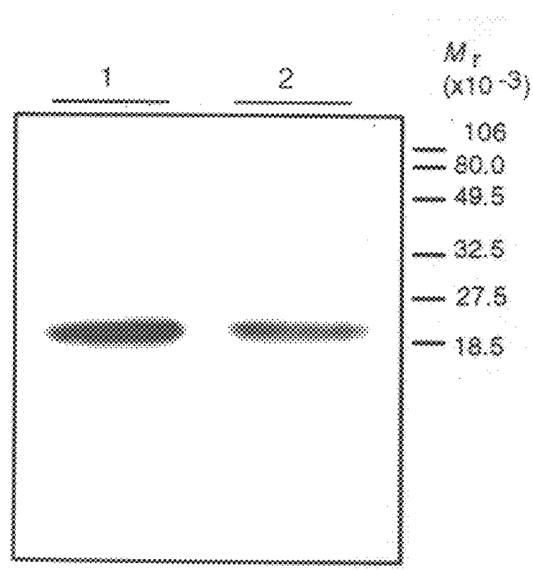
FIG. 4A shows N-deglycosylation of the protein encoded by the cloned MAFA cDNA. $10^7$ transfected COS-7 cells were surface-radioiodinated, and the derived lysate was incubated with mAb G63-coated beads. The beads were then washed and incubated with N-glycosidase F as described in Experimental Procedures. In parallel, a sample of MAFA immunoprecipitated from surface-radioiodinated RBL-2H3 cells was N-deglycosylated following the same procedure. The immunoprecipitates were then subjected to reducing SDS-PAGE on a 15% polyacrylamide gel, and electrotransferred to a nitrocellulose membrane. The membrane was then autoradiographed.
Figure 4B:
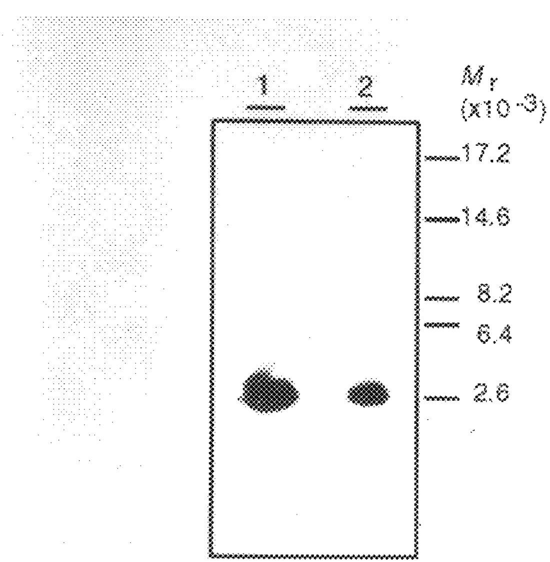
FIG. 4B shows endoproteinase Lys-C digestion of both the protein encoded by the cloned cDNA and the MAFA. The nitrocellulose strips containing the 20 kDa polypeptide cores visualized in FIG. 4A were excised from the membrane and incubated with endo-proteinase Lys-C as described in Experimental Procedures. The peptides derived from the MAFA and the protein expressed by the transfected COS-7 cells were then eluted and subjected to electrophoresis in a tricine-SDS-polyacrylamide gel that was dried and autoradiographed.

In order to determine the apparent molecular mass of the recombinant protein expressed by COS-7 cells transfected with the cloned cDNA, and to deduce its relation to the MAFA expressed by RBL-2H3 cells, monolayers of $10^7$ transfected and control, untransfected COS-7 cells were surface radioiodinated followed by lysis and immunoprecipitation with G63-coated beads (cf. Experimental Procedures). The immunoprecipitates, eluted by boiling in sample buffer, were subjected to SDS-PAGE and the gel was dried and autoradiographed (FIG. 3 B). mAb G63 immunoprecipitated from the transfected cells' lysates a single labeled species with an apparent Mr of 58 kDa under non-reducing conditions and 28 kDa under reducing conditions. The slight difference between Mr of the respective proteins isolated from the RBL-2H3 and transfected cells might be due to differences in post-translational modifications. Therefore, the apparent molecular mass of the respective N-deglycosylated polypeptide chains were compared. Lysates from surface-radioiodinated RBL-2H3 cells and COS-7 cells transfected with the cloned cDNA were incubated with mAb G63-coated beads. The immunoprecipitates were N-deglycosylated, eluted by boiling in SDS-PAGE sample buffer and analyzed by electrophoresis under reducing conditions. Both protein samples were shown by autoradiography (FIG. 4A) to have a 20 kDa polypeptide core, further suggesting that the cloned protein is, indeed, MAFA. To substantiate this point, both 20 kDa polypeptides shown in FIG. 4A were digested in parallel with endoproteinase Lys-C. Analysis of the resulting peptide fragments by tricine-SDS gel electrophoresis and autoradiography revealed in both cases a single radioactively labeled peptide of 2.6 kDa (FIG. 4 B). Taken together, these results strongly support that the cloned cDNA sequence indeed codes for the MAFA.

EXAMPLE 4

Determination of the MAFA cDNA Sequence

The complete nucleotide sequence of the MAFA cDNA is depicted in FIG. 5 (SEQ ID NO:4). An open reading frame deduced from the nucleotide sequence starts at nucleotide #54 with a codon for methionine and ends at nucleotide #617 before a TGA stop codon.

A search for homology to the MAFA cDNA nucleotide sequence did not reveal any significant result, indicating that the MAFA might be encoded by an unknown gene. However, when the search was done at the amino acid level, significant homology was found between the C-terminal 114 amino acids of the MAFA and the carbohydrate recognition domain (CRD) of several type II integral membrane proteins which are members of the $Ca^{2+}$-dependent animal lectin family (Drickamer and Taylor, 1993). Among them, two hepatic lectins: the murine asialoglycoprotein receptor 2 (Sanford and Doyle, 1990) and the rat Kupffer cell receptor (Hoyle and Hill, 1988). Interestingly, the other C-type lectins displaying high sequence homology with the MAFA CRD are all involved in immunological functions. These are the type II receptor for IgE (FcϵRII/CD23) (Bettler et al., 1989), the natural killer antigen NKR-P1 (Giorda and Trucco, 1991), the T-cell early activation antigen CD69 (Hamann et al., 1993), the B-cell differentiation antigen CD72 (von Hoegen et al., 1990), and Ly-49, an NK cell receptor to MHC class I alloantigens (Chan and Takei, 1989). Amino acid sequence alignment of the CRD's of the MAFA and of several of the latter lectins shows the absolute conservation of 15 residues (6 cysteines, 5 tryptophans, and 2 glycines and leucins) interspersed within this 114 to 129 amino acids long domain (FIG. 6). Furthermore, the Trp-Ile-Gly-Leu (residues 58–61 of SEQ ID NO:6) and Cys-Tyr-Tyr-Phe (residues 12–15 of SEQ ID NO:6) motifs are highly conserved throughout these proteins.

The Kyte-Doolittle hydropathy plot (Yokoyama et al., 1989) of the deduced amino acid sequence predicts a 21 amino acids long transmembrane domain (FIG. 5, underlined). A search for consensus amino acid sequences with the Motifs application of the GCG package revealed two putative N-glycosylation sites located within the CRD. In addition, a putative casein kinase II phosphorylation site was found in the cytoplasmic domain on serine 8. Significantly, serine 8 is part of a tyr-ser-thr-leu (residues 7–10 of SEQ ID NO:5) sequence, and related Tyr-Xaa-Xaa-Leu/Ile (SEQ ID NO:12) motifs were observed in the cytoplasmic domain of several type II integral membrane proteins of the C-type animal lectin family (Table 1). The leucine residue located (in most cases) three amino acids carboxyl-terminal to each of the tyrosines also appears to be essential for that motif's function (Samelson and Klausner, 1992).

Significantly, a tyrosine containing sequence (Tyr-Ser-Leu-Leu) (SEQ ID NO:13), hereinafter YSLL, is present in the cytoplasmic domain of the mouse FcγRIIb1 and FcγRIIb2. The tyrosyl residue present in this sequence was shown to be essential for the FcγRIIb2-mediated endocytosis and phagocytosis in mast cells (Daeron et al., 1993). An identical tyrosine containing motif (YSLL) was found in FcγRII of rat origin (Bocek and Pecht, 1993). This YSLL sequence in human FcγRIIB was shown to be involved in the abrogation of B cell activation triggered by membranal Ig crosslinking (Muta et al., 1994). Co-clustering of the FcγRIIB and the BCR leads to the phosphorylation of the tyrosyl in the YSLL sequence, $Ca^2$+ influx blockage and arrest of the cellular activation (Muta et al., 1994). In the following example we examined whether the MAFA phosphorylation state is affected by FcεRI and the MAFA clustering.

TABLE 1

Presence of tyrosine-based tetrapeptide motifs in type II transmembrane C-type lectins

| C-type lectin | tyrosine-based motif |
|---|---|
| chicken hepatic lectin | tyr—val—leu—leu SEQ ID NO: 14 |
| human asialoglycoprotein receptor | tyr—glu—asp—leu SEQ ID NO: 15 |
| human type II FceR | tyr—ser—glu—ile SEQ ID NO: 16 |
| human CD72 | tyr—ala—asp—leu SEQ ID NO: 17 |
| mouse Ly49B | tyr—thr—thr—leu SEQ ID NO: 18 |
| rat NKR-P1 | tyr—leu—ser—leu SEQ ID NO: 19 |
| mouse NKR-P1 | tyr—phe—gly—leu SEQ ID NO: 20 |

EXAMPLE 5

Phosphoamino Acid Analysis of the MAFA

Figure 7:
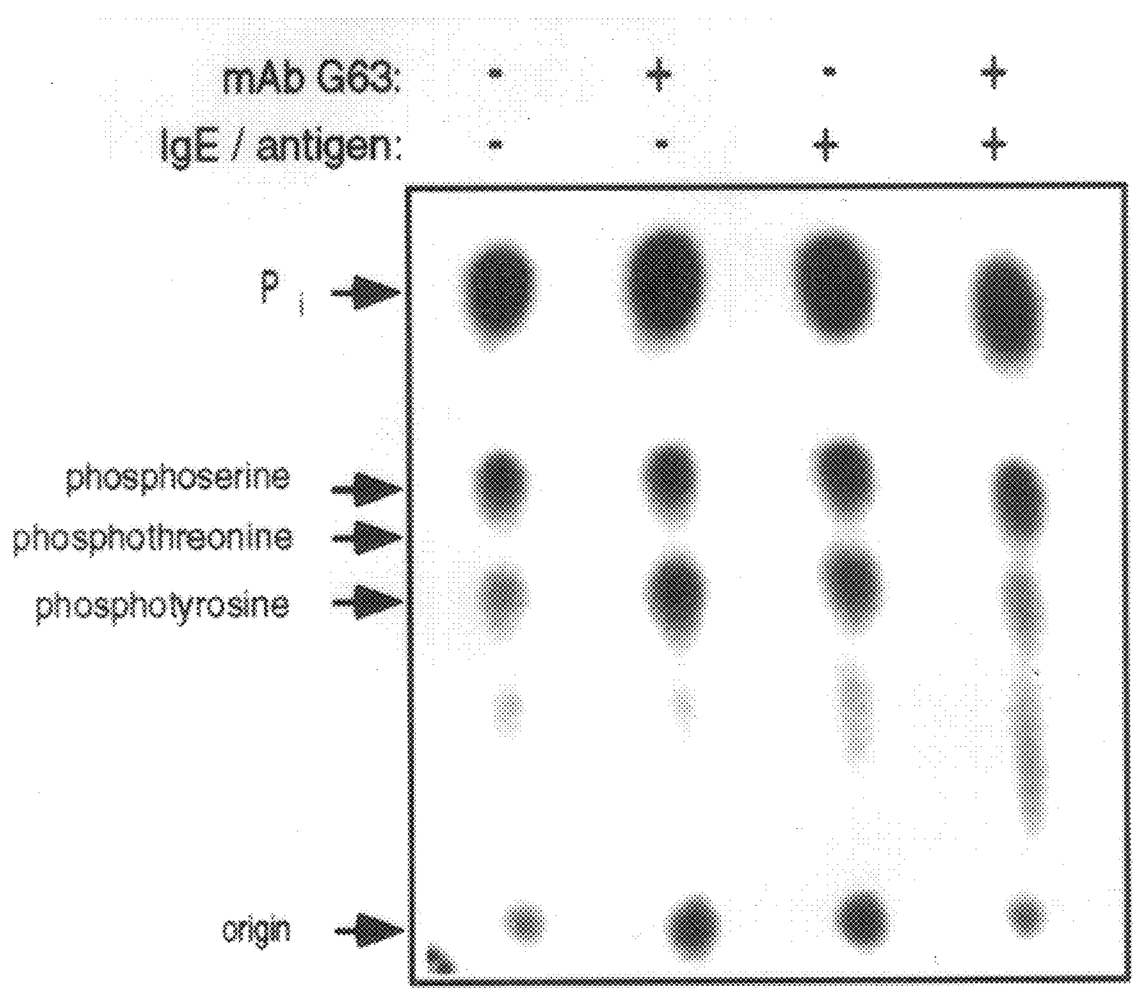
FIG. 7 shows phosphoamino acid analysis of the $^{32}P$-labeled MAFA. PVDF stripes containing 20 kDa radiolabeled MAFA were excised, washed and heated to 110° C. in 6 N HCl for one hour. The HCl was then removed by evaporation and the hydrolysates were resuspended in 5 $\mu$l pH 3.5 buffer, loaded on 10×10 cm cellulose-coated glass plates, and separated by electrophoresis. 1 $\mu$g non-radioactive phosphoserine, phosphothreonine and phosphotyrosine were used as internal standards and visualized by ninhydrin staining. The radioactive phosphoamino acids were detected by autoradiography. The treatment for each sample is indicated below their loading points.

Phosphoamino acid analysis of the MAFA was undertaken in samples derived from resting and FcεRI stimulated cells, both in the presence and the absence of MAFA clustering by mAb G63. RBL-2H3 cells, cultured in medium containing $^{32}$P-labeled orthophosphate, were IgE saturated by the presence of 10 nM of a DNP-specific mouse monoclonal antibody and stimulated for 2 minutes by the addition of 100 μg/ml DNP11-BSA. The effect of the MAFA clustering was examined by the addition of 10 nM mAb G63 to the cells 10 minutes prior to lysis (non-stimulated cells) or to the addition of antigen (activated cells). G63-immunoprecipitates from the lysates were first incubated with N-glycosidase F and then eluted and separated through a 15% SDS-polyacrylamide gel under reducing conditions. The proteins were then electrotransferred to a PVDF membrane and visualized by autoradiography (not shown). The 20 kDa N-deglycosylated MAFA contained in the PVDF strips was then hydrolyzed by heating to 110° C. in 6 N HCl for 1 hour. The phosphoamino acids were separated by electrophoresis on cellulose-coated plates, which were then autoradiographed (FIG. 7). The location of the control phosphoserine, phosphothreonine and phosphotyrosine was determined by ninhydrin staining. No $^{32}$P labeled phosphothreonine could be observed in any of the samples. In contrast, similar amounts of radioactive phosphoserine and phosphotyrosine were found in samples derived from resting cells, indicating that the MAFA is constitutively phosphorylated on both seryl and tyrosyl residues. Antigen stimulation of RBL-2H3 cells, as well as their incubation in the presence of mAb G63, slightly increased the intensity of phosphorylation of both these residues. However, the increase in the level of tyrosyl phosphorylation in cell samples where both FcεRI and the MAFA were clustered by antigen and mAb G63, respectively, was reduced, displaying an intensity similar to that observed in resting cells. These results suggest that mAb G63 might exert its inhibitory effect on RBL-2H3 cells' response to antigenic stimulation via the reduction in the MAFA's tyrosyl (residue 7) phosphorylation.

EXAMPLE 6

Transcription of the MAFA Gene in Different Rat Organs

Figure 8:
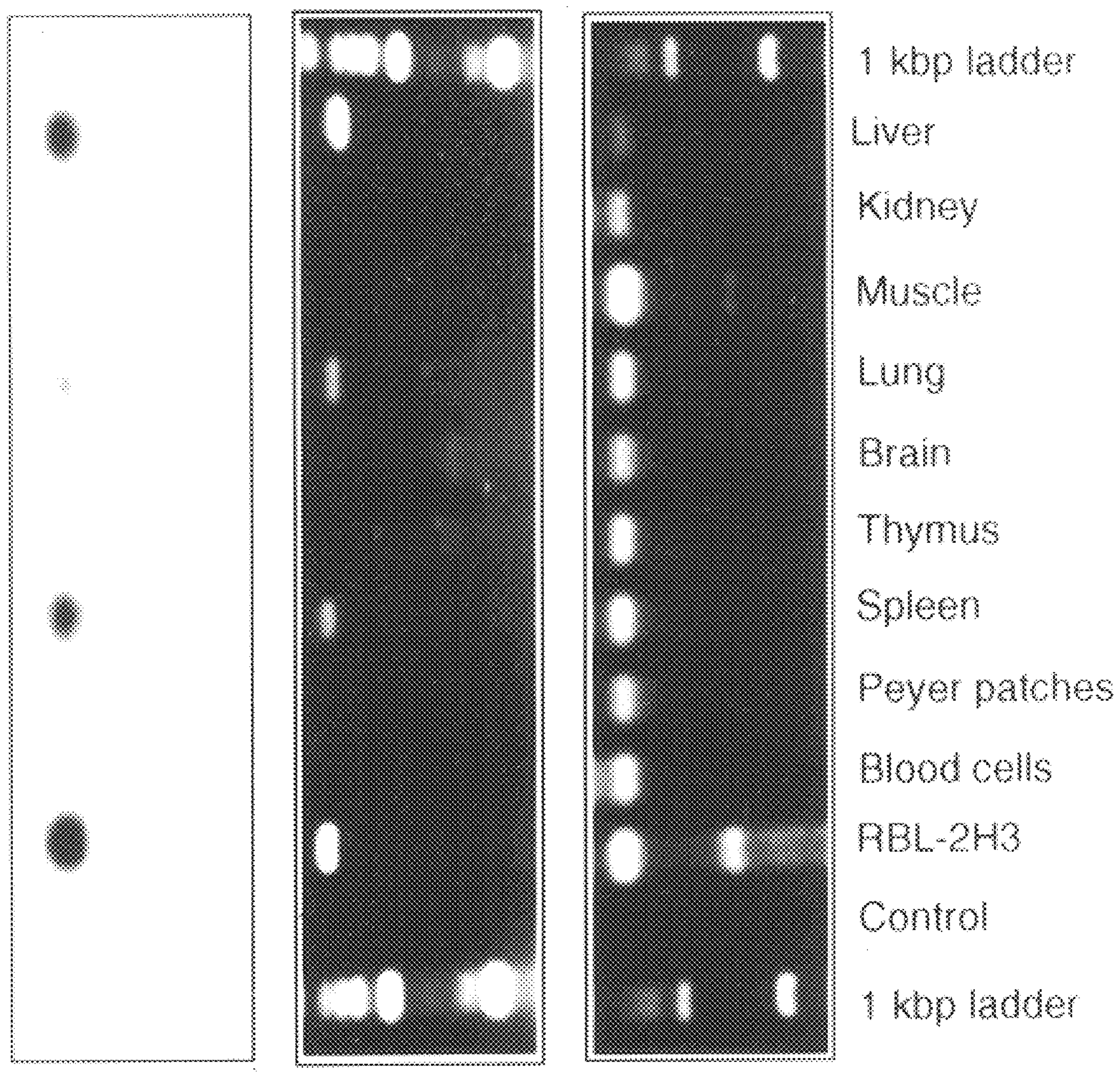
FIG. 8 shows reverse transcription-PCR analysis of MAFA expression. Total RNA (2 $\mu$g) derived from the indicated rat tissues and from RBL-2H3 cells were reverse transcribed in a reaction mixture containing both β-actin and MAFA-specific primers. One third of the cDNA was used as a template in either a β-actin (panel A) or a MAFA (panel B) oligonucleotides-primed PCR reaction. One tenth of each PCR reaction mixture was analyzed by electrophoresis through 1% agarose gels. The DNA of the gel shown in panel B was transferred to a nylon membrane, probed with a MAFA-specific internal oligonucleotide in an hybridization solution containing 20% formamide. The membrane was then washed in 0.2×SSC, 0.1% SDS and autoradiographed for 2 hours (panel C).

Reverse transcription-polymerase chain reaction is a combined method which allows a very sensitive detection of the presence of a given sequence in a relatively small sample of RNA. 2 μg of total RNA derived from rat liver, kidney, muscle, lung, brain, thymus, spleen, Peyer's patches, blood cells and from RBL-2H3 cells were reverse transcribed in reactions primed by both MAFA and β-actin-derived primers (Pinkas-Kramarski et al., 1994). One third of the produced single standard cDNA was used as a template for each of two PCR reactions designed to amplify β-actin and MAFA-derived sequences, respectively. Upon completion of the reaction, 10 μl were withdrawn for electrophoresis through a 1.2% agarose gel (FIG. 8, panels A and B). β-actin-derived amplification products were obtained from all the samples tested (FIG. 8, panel A). On the other hand, only the liver, lung and spleen-derived samples, in addition to that derived from RBL-2H3 cells, yielded MAFA-derived amplification products of the expected size, i.e. 308 bp (FIG. 8, panel B). The possibility of these being the product of genomic DNA amplification was excluded by the presence of a large intron between sites of annealing of the chosen primers. The DNA was then transferred to a nylon membrane, which was probed with an internal MAFA-derived oligonucleotide. As can be seen in FIG. 8, panel C, the probe hybridized to the 308 bp long amplification products. However, when the blot was overexposed, the presence of MAFA-derived PCR products was also detectable in the other samples as well (not shown), indicating that although MAFA transcripts are readily detectable in the mentioned rat organs, very small amounts appear to be present also in the other examined organs (i.e. kidney, muscle, brain, thymus, peyer patches and blood cells).

References

1. Barsumian, E. L., Isersky, C., Petrino, M. G. and Siraganian, R. P. (1981). IgE induced histamine release from rat basophilic cell lines: isolation of releasing and non-releasing clones. Eur. J. Immunol., 11, 317–323.
2. Beaven, M. A., Moore, J. P., Smith, G. A., Hesketh, T. R. and Metcalfe, J. C. (1984a). The calcium signal and phosphatidylinositol breakdown in RBL-2H3 cells. J. Biol. Chem., 259, 7137–7142.
3. Beaven, M. A., Rogers, J., Moore, J. P., Hesketh, T. R., Smith, G. A. and Metcalfe, J. C. (1984b). The mechanism of calcium signal and correlation of histamine release in 2H3 cells. J. Biol. Chem., 259, 7129–7136.

4. Benhamou, M., Gutkind, J. S., Robbins, K. C. and Siraganian, R. P. (1990). Tyrosine phosphorylation coupled to IgE receptor-mediated signal transduction and histamine release. Proc. Natl. Acad. Sci. USA, 87, 5327–5330.

5. Benhamou, M., Stephan, V., Robbins, K. C. and Siraganian, R. P. (1992). High-affinity IgE receptor-mediated stimulation of rat basophilic leukemia (RBL-2H3) cells induces early and late protein-tyrosine phosphorylations. J. Biol. Chem., 267, (11) 7310–7314.

6. Bettler, B., Hofstetter, H., Rao, M., Yokoyama, W. M., Kilchherr, F. and Conrad, D. H. (1989). Molecular structure and expression of the murine lymphocyte low-affinity receptor for IgE (FceRII). Proc. Natl. Acad. Sci. USA, 86, 7566–7570.

7. Bocek, P. and Pecht, I. (1993). Cloning and sequence of the cDNA coding for rat type II Fcγ (receptor of mast cells. FEBS letters, 331, 86–90.

8. Bradding, P., Feather, I. H., Wilson, S., Bardin, P. G., Heusser, C. H., Holgate, S. T. and Howarth, P. H. (1993). Immunolocalization of cytokines in the nasal mucosa of normal and perenial rhinitic subjects. The mast cell as a source of IL-4, IL-5 and IL-6 in human alergic mucosal inflammation. J. Immunol., 151, 3853–3865.

9. Caras, I. W., Weddell, G. N., Davitz, M. A., Nussenzweig, V. and Martin, D. W. Jr. (1987) Signal for attachment of a phospholipid membrane anchor in decay accelerating factor. Science 238: 1280–1283.

10. Chan, P. -Y. and Takei, F. (1989). Molecular cloning and characterization of a novel murine T cell surface antigen, YE1/48. J. Immunol., 142, 1727–1736.

11. Daeron, M., Malbec, O., Latour, S., Bonnerot, C., Segal, D. M. and Fridman, W. H. (1993). Distinct intracytoplasmic sequences are required for endocytosis and phagocytosis via murine Fc gamma RII in mast cells. Int. Immunol., 5, (11) 1393–1401.

12. Drickamer, K. and Taylor, M. E. (1993). Biology of animal lectins. Annu. Rev. Cell Biol., 9, 237–264.

13. Eiseman, E. and Bolen, J. B. (1992). Engagement of the high-affinity IgE receptor activates src protein-related tyrosine kinases. Nature, 355, (6355) 78–80.

14. Elder, J. H., Pickett II, R. A., Hampton, J. and Lerner, R. A. (1977). Radioiodination of Proteins in Single Polyacrylamide Gel Slices. J. Biol. Chem., 252, 6510–6515.

15. Fernandez, J., DeMott, M., Atherton, D. and Mische, S. M. (1992). Internal protein sequence analysis: enzimatic digestion for less than 10 mg of protein bound to polyvinilidene difluoride or nitrocellulose membranes. Anal. Biochem., 201, 255–264.

16. Galli, S. J., Gordon, J. R. and Wershil, B. K. (1991). Cytokine production by mast cells and basophils. Curr. Opin. Immunol., 3, 865–873.

17. Gearing, D. P., King, J. A., Gough, N. M. and Nicola, N. A. (1989). Expression cloning of a receptor for human granulocyte-macrophage colony-stimulating factor. EMBO J., 8, 3667–3676.

18. Giorda, R. and Trucco, M. (1991). Mouse NKR-P1. A family of genes selectively coexpressed in adherent lymphokine-activated killer cells. J. Immunol., 147, 1701–1708.

19. Gonda, T. J., Sheiness, D. K. and Bishop, J. M. (1982). Transcripts from the cellular homologs of retroviral oncogenes: distribution among chicken tissues. Mol. Cell. Biol., 2, 617–624.

20. Gubler, U. and Hoffman, B. J. (1983). A simple very efficient method for generating cDNA libraries. Gene, 25, 263–269.

21. Hamann, J., Fiebig, H. and Strauss, M. (1993). Expression cloning of the early activation antigen CD69, a type II integral membrane protein with a C-type lectin domain. J. Immunol., 150, (11) 4920–4927.

22. Hampe, C. S. and Pecht, I. (1994). Protein tyrosine phosphatase activity enhancement is induced upon Fce receptor activation of mast cells. FEBS Lett., 346, 194–198.

23. Hoyle, G. W. and Hill, R. L. (1988). Molecular cloning and sequencing of a cDNA for a carbohydrate binding receptor unique to rat Kupffer cells. J. Biol. Chem., 263, 7487–7492.

24. Jin, J. J., Nikitin, A. Y. and Rajewsky, M. F. (1993). Cell Growth Differ., 4, 227–237.

25. Li, W., Deanin, G. G., Margolis, B., Schlessinger, J. and Oliver, J. (1992) FcεRI-mediated tyrosine phosphorylation of multiple proteins, including phospholipase Cγ1 and the receptor βγ2 complex, in RBL-2H3 rat basophilic leukemia cells. Mol. Cell. Biol. 12: 3176–3182.

26. Lin, H. Y., Kaji, E. H., Winkel, G. K., Ives, H. I. and Lodish, H. F. (1991). Cloning and functional expression of a vascular smooth muscle endothelin 1 receptor. Proc. Natl. Acad. Sci. USA, 88, 3185–3189.

27. Marchalonis, J. J. (1966). An enzymatic method for the trace iodination of immunoglobulins and other proteins. Biochem. J., 113, 299.

28. Muta, T., Kurosaki, T., Misulovin, Z., Sanchez, M., Nussenzweig, M. C. and Ravetch, J. V. (1994). A 13-amino-acid motif in the cytplasmic domain of the FcγRIIB modulates B-cell receptor signalling. Nature, 368, 70–73.

29. Nagai, K. and Thogersen, H. C. (1987) "Synthesis and sequence-specific proteolysis of hybrid proteins produced in *Escherichia coli*" Methods Enzymol. 153: 461–481.

30. Ortega, E., Hazan, B., Zor, U. and Pecht, I. (1989). Mast cell stimulation by monoclonal antibodies specific for the IgE receptor yields distinct responses of arachidonic acid and leukotriene C4 secretion. Eur. J. Immunol., 19, 2251–2256.

31. Ortega, E. and Pecht, I. (1988). A monoclonal antibody that inhibits secretion from rat basophilic leukemia cells and binds to a novel membrane component. J. Immunol., 141, 4324–4332.

32. Ortega, E., Schneider, H. and Pecht, I. (1991). Possible interactions between the Fcε receptor and a novel mast cell function-associated antigen. Int. Immunol., 3, 333–342.

33. Ortega, E., Schweitzer-Stenner, R. and Pecht, I. (1988). Possible orientational constraints determine secretory signals induced by aggregation of IgE receptors on mast cells. EMBO J., 7, 4101–4109.

34. Pinkas-Kramarski, R., Eilam, R., Spiegler, O., Lavi, S., Liu, N., Chang, D., Wen, D., Schwartz, M. and Yarden, Y. (1994). Brain neurons and glial cells express Neu differentiation factor/heregulin: a survival factor for astrocytes. Proc. Natl. Acad. Sci. USA, 91, 9387–9391.

35. Sambrook, J., Fritsch, E. F. and Maniatis, T. (1989). Molecular cloning: A laboratory manual. Cold Spring Harbor Laboratory Press.

36. Samelson, L. E. and Klausner, R. D. (1992). Tyrosine kinases and tyrosine-based activation motifs Current research on activation through the T cell antigen receptor. J. Biol. Chem., 267, 24913–24916.

37. Sanford, J. P. and Doyle, D. (1990). Mouse asialoglycoprotein receptor cDNA sequence: conservation of receptor genes during mammalian evolution. Biochim. Biophys. Acta, 1087, 259–261.

38. Schagger, H. and von Jagow, G. (1987). Tricine-sodium dodecyl sulfate-polyacrylamide gel electrophoresis for the separation of proteins in the range from 1 to 100 kDa. Anal. Biochem., 166, 368–379.

39. Seed, B. and Aruffo, A. (1987). Molecular cloning of the CD2 antigen, the T-cell erythrocyte receptor, by a rapid immunoselection procedure. Proc. Natl. Acad. Sci. USA, 84, 3365–3369.

40. von Hoegen, I., Nakayama, E. and Parnes, J. R. (1990). Identification of a human protein homologous to the mouse Lyb-2 B cell differentiation antigen and sequence of the corresponding CDNA. J. Immunol., 144, 4870–4877.

41. Yokoyama, W. M., Jacobs, L. B., Kanagawa, O., Shevach, E. M. and Cohen, D. I. (1989). A murine T lymphocyte antigen belongs to a supergene family of type II integral membrane proteins. J. Immunol., 143, 1379–1386.

What is claimed is:

1. An isolated DNA molecule comprising a nucleotide sequence selected from the group consisting of:

(a) a nucleotide sequence which encodes a mammalian mast cell function-associated antigen (MAFA) monomer having the amino acid sequence of SEQ ID NO:5; and (b) a nucleotide sequence which encodes the extracellular domain of MAFA, having amino acids 55–188 of SEQ ID NO:5.

2. An isolated DNA molecule in accordance with claim 1, comprising a nucleotide sequence which encodes a MAFA monomer having the amino acid sequence of SEQ ID NO:5.

3. An isolated DNA molecule in accordance with claim 2, comprising the nucleotide sequence of nucleotides 54–617 of SEQ ID NO:4.

4. An isolated DNA molecule in accordance with claim 1, comprising a nucleotide sequence which encodes the extracellular domain of MAFA, having the amino acid sequence of amino acids 55–188 of SEQ ID NO:5.

5. An isolated DNA molecule in accordance with claim 4, comprising the nucleotide sequence of nucleotides 216–617 of SEQ ID NO:4.

6. A recombinant expression vector comprising a DNA coding sequence in accordance with claim 1.

7. A host cell containing a recombinant expression vector in accordance with claim 6.

8. A process for preparing a mammalian MAFA, or the extracellular domain thereof, comprising culturing a host cell according to claim 7 under conditions promoting expression, and isolating the molecule expressed thereby.

9. A polypeptide comprising the extracellular domain of a mammalian mast cell function-associated antigen (MAFA) monomer of the sequence of residues 55–188 of SEQ ID NO:5.

10. A method for identifying and isolating potential ligands of the mammalian mast cell function-associated antigen (MAFA), comprising:

(i) attaching a polypeptide in accordance with claim 9 to a suitable matrix;

(ii) bringing a potential ligand into contact with said matrix-bound polypeptide;

(iii) determining whether or not said potential ligand is bound by said matrix-bound polypeptide; and (iv) if said potential ligand binds to said matrix bound polypeptide, identifying said potential ligand as a ligand and isolating said ligand.

* * * * *

SEQUENCE LISTING

```
(1) GENERAL INFORMATION:

   (iii) NUMBER OF SEQUENCES: 20


(2) INFORMATION FOR SEQ ID NO: 1:

     (i) SEQUENCE CHARACTERISTICS:
          (A) LENGTH: 18 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO: 1:

GCCACTGTTA CTACTTCT                                                    18


(2) INFORMATION FOR SEQ ID NO: 2:

     (i) SEQUENCE CHARACTERISTICS:
          (A) LENGTH: 18 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO: 2:

GACCTTCTCA CAGATCCA                                                    18


(2) INFORMATION FOR SEQ ID NO: 3:

     (i) SEQUENCE CHARACTERISTICS:
          (A) LENGTH: 17 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO: 3:

GGAGTATGTG GGCGAGG                                                     17


(2) INFORMATION FOR SEQ ID NO: 4:

     (i) SEQUENCE CHARACTERISTICS:
          (A) LENGTH: 1461 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION:54..617

    (xi) SEQUENCE DESCRIPTION: SEQ ID NO: 4:

CACCCTGCTT ACTGTCGTCA CTCCCTGCTG AGTGTGAAGG GCGTTGGGTG GAG ATG          56
                                                           Met
                                                             1
```

```
GCC GAC AAC TCT ATC TAC TCA ACA TTA GAG CTG CCT GCT GCA CCT CGA      104
Ala Asp Asn Ser Ile Tyr Ser Thr Leu Glu Leu Pro Ala Ala Pro Arg
              5                  10                  15

GTC CAA GAT GAC TCC AGA TGG AAG GTC AAA GCT GTC TTA CAC CGA CCC      152
Val Gln Asp Asp Ser Arg Trp Lys Val Lys Ala Val Leu His Arg Pro
         20                  25                  30

TGT GTT TCC TAC CTT GTG ATG GTG GCT TTG GGG CTT TTG ACT GTG ATT      200
Cys Val Ser Tyr Leu Val Met Val Ala Leu Gly Leu Leu Thr Val Ile
     35                  40                  45

CTC ATG AGT CTA CTG TTG TAC CAA CGG ACT CTG TGC TGT GGC TCC AAG      248
Leu Met Ser Leu Leu Leu Tyr Gln Arg Thr Leu Cys Cys Gly Ser Lys
 50                  55                  60                  65

GGC TTT ATG TGT TCC CAG TGC TCC AGG TGC CCC AAC CTC TGG ATG AGG      296
Gly Phe Met Cys Ser Gln Cys Ser Arg Cys Pro Asn Leu Trp Met Arg
                 70                  75                  80

AAC GGG AGC CAC TGT TAC TAC TTC TCA ATG GAG AAA AGG GAC TGG AAC      344
Asn Gly Ser His Cys Tyr Tyr Phe Ser Met Glu Lys Arg Asp Trp Asn
             85                  90                  95

TCT AGT CTG AAG TTC TGT GCA GAC AAA GGC TCG CAT CTC CTT ACA TTT      392
Ser Ser Leu Lys Phe Cys Ala Asp Lys Gly Ser His Leu Leu Thr Phe
        100                 105                 110

CCG GAC AAC CAG GGA GTG AAC CTG TTC CAG GAG TAT GTG GGC GAG GAC      440
Pro Asp Asn Gln Gly Val Asn Leu Phe Gln Glu Tyr Val Gly Glu Asp
    115                 120                 125

TTT TAC TGG ATT GGC TTG AGG GAC ATC GAT GGC TGG AGG TGG GAA GAT      488
Phe Tyr Trp Ile Gly Leu Arg Asp Ile Asp Gly Trp Arg Trp Glu Asp
130                 135                 140                 145

GGC CCA GCT CTC AGC TTA AGC ATT CTC TCT AAC AGC GTG GTA CAG AAG      536
Gly Pro Ala Leu Ser Leu Ser Ile Leu Ser Asn Ser Val Val Gln Lys
                150                 155                 160

TGT GGC ACC ATC CAC AGG TGT GGC CTC CAC GCC TCC AGT TGT GAG GTT      584
Cys Gly Thr Ile His Arg Cys Gly Leu His Ala Ser Ser Cys Glu Val
            165                 170                 175

GCT TTG CAG TGG ATC TGT GAG AAG GTC CTG CCC TGAAGGATTC CACTGTGTCC    637
Ala Leu Gln Trp Ile Cys Glu Lys Val Leu Pro
        180                 185

CAAGCCTCAG ATCTGCCACA TGTCTTCAAA AAGAGGGAAT GGGCATGGGG AACCTCTGTT    697

CACAAAGGTG TCTTTAGCAA ATGCCAAACC TGTTATGATA TGCCATTAGA CAGGCGTTAG    757

CATTCCTTCC TGGGAGCTGG CATTTTTCAA CTGGGCTTTC TCAGTCATGT TAGCCATTTA    817

AAGCCTAAAT CTGGGCAAAT GAAATAGATA AAATTTATTT TGATGGCTCT TACTGCACAA    877

ACTCACCCTG GCTTTCTCAT CCCATACTCT GCCATATCTA TCAAAGATAT GTGCAAAACT    937

ATTCATCTGC AGAAGAACCC CCACCACGGT CAATAACACA TTACATAGAC ATCGAATAGA    997

GACAGAAAAG CAAACACCTC CTGTTCTCAC TCCTGCTTGG AAGCTGAAGT AGCTCAAGCC   1057

TGAGGTGTAG GGAGAAGTGC AGTGGTTACC AGAGTCCAGG AGACTGAAGG GATGGTAGAG   1117

GTTGGTTAAT GGTTTGGCTG GTGTGGGGTG ACCATCATGA TTAATGATTG TTGTATGTTT   1177

GCCAATATGT TGTGAACTTC CGGATAGCGA GGTGGAAGGA CCGTGGGTGT TACCAAATGC   1237

CTGCAGGAGA GATGTGCTGA GAACCCTGAC TGGATGATTT CCACACACAT TGAAATATCA   1297

CACTGTGCCC CATAAATGTG TACAATCATT ATCTATCCCT AATTTCCCTA AAAATTAAAG   1357

AAGTCCCAAT TAAAATAAAA AATACCTTTC TGCTAAAAAA AAAAAAAAAA AAAAAAAAAA   1417

AAAAAAAAAA AAAAAAAAAA AAAAAAAAAA AAAAAAAAAA AAAA                    1461
```

(2) INFORMATION FOR SEQ ID NO: 5:

(i) SEQUENCE CHARACTERISTICS:

(A) LENGTH: 188 amino acids
(B) TYPE: amino acid
(D) TOPOLOGY: linear (ii) MOLECULE TYPE: protein (xi) SEQUENCE DESCRIPTION: SEQ ID NO: 5:

```
Met Ala Asp Asn Ser Ile Tyr Ser Thr Leu Glu Leu Pro Ala Ala Pro
  1               5                  10                  15

Arg Val Gln Asp Asp Ser Arg Trp Lys Val Lys Ala Val Leu His Arg
             20                  25                  30

Pro Cys Val Ser Tyr Leu Val Met Val Ala Leu Gly Leu Leu Thr Val
         35                  40                  45

Ile Leu Met Ser Leu Leu Leu Tyr Gln Arg Thr Leu Cys Cys Gly Ser
     50                  55                  60

Lys Gly Phe Met Cys Ser Gln Cys Ser Arg Cys Pro Asn Leu Trp Met
 65                  70                  75                  80

Arg Asn Gly Ser His Cys Tyr Tyr Phe Ser Met Glu Lys Arg Asp Trp
                 85                  90                  95

Asn Ser Ser Leu Lys Phe Cys Ala Asp Lys Gly Ser His Leu Leu Thr
            100                 105                 110

Phe Pro Asp Asn Gln Gly Val Asn Leu Phe Gln Glu Tyr Val Gly Glu
        115                 120                 125

Asp Phe Tyr Trp Ile Gly Leu Arg Asp Ile Asp Gly Trp Arg Trp Glu
    130                 135                 140

Asp Gly Pro Ala Leu Ser Leu Ser Ile Leu Ser Asn Ser Val Val Gln
145                 150                 155                 160

Lys Cys Gly Thr Ile His Arg Cys Gly Leu His Ala Ser Ser Cys Glu
                165                 170                 175

Val Ala Leu Gln Trp Ile Cys Glu Lys Val Leu Pro
            180                 185
```

(2) INFORMATION FOR SEQ ID NO: 6:

(i) SEQUENCE CHARACTERISTICS:
(A) LENGTH: 114 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 6:

```
Cys Pro Asn Leu Trp Met Arg Asn Gly Ser His Cys Tyr Tyr Phe Ser
1               5                   10                  15

Met Glu Lys Arg Asp Trp Asn Ser Ser Leu Lys Phe Cys Ala Asp Lys
            20                  25                  30

Gly Ser His Leu Leu Thr Phe Pro Asp Asn Gln Gly Val Asn Leu Phe
        35                  40                  45

Gln Glu Tyr Val Gly Glu Asp Phe Tyr Trp Ile Gly Leu Arg Asp Ile
    50                  55                  60

Asp Gly Trp Arg Trp Glu Asp Gly Pro Ala Leu Ser Leu Ser Ile Leu
65                  70                  75                  80

Ser Asn Ser Val Val Gln Lys Cys Gly Thr Ile His Arg Cys Gly Leu
                85                  90                  95

His Ala Ser Ser Cys Glu Val Ala Leu Gln Trp Ile Cys Glu Lys Val
            100                 105                 110

Leu Pro
```

(2) INFORMATION FOR SEQ ID NO: 7:

(i) SEQUENCE CHARACTERISTICS:
(A) LENGTH: 125 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 7:

```
Cys Pro Lys Asn Trp Leu His Phe Gln Gln Lys Cys Tyr Tyr Phe Gly
1               5                   10                  15

Lys Gly Ser Lys Gln Trp Ile Gln Ala Arg Phe Ala Cys Ser Asp Leu
            20                  25                  30

Gln Gly Arg Leu Val Ser Ile His Ser Gln Lys Glu Gln Asp Phe Leu
        35                  40                  45

Met Gln His Ile Asn Lys Lys Asp Ser Trp Ile Gly Leu Gln Asp Leu
    50                  55                  60

Asn Met Glu Gly Glu Phe Val Trp Ser Asp Gly Ser Pro Val Gly Tyr
65                  70                  75                  80

Ser Asn Trp Asn Pro Gly Glu Pro Asn Asn Gly Gly Gln Gly Glu Asp
                85                  90                  95

Cys Val Met Met Arg Gly Ser Gly Gln Trp Asn Asp Ala Phe Cys Arg
            100                 105                 110

Ser Tyr Leu Asp Ala Trp Val Cys Glu Gln Leu Ala Thr
        115                 120                 125
```

(2) INFORMATION FOR SEQ ID NO: 8:

(i) SEQUENCE CHARACTERISTICS:
(A) LENGTH: 115 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 8:

```
Cys Ser Glu Asp Trp Val Gly Tyr Gln Arg Lys Cys Tyr Phe Ile Ser
1               5                   10                  15

Thr Val Lys Arg Ser Trp Thr Ser Ala Gln Asn Ala Cys Ser Glu His
            20                  25                  30

Gly Ala Thr Leu Ala Val Ile Asp Ser Glu Lys Asp Met Asn Phe Leu
        35                  40                  45

Lys Arg Tyr Ala Gly Arg Glu Glu His Trp Val Gly Leu Lys Lys Glu
    50                  55                  60

Pro Gly His Pro Trp Lys Trp Ser Asn Gly Lys Glu Phe Asn Asn Trp
65                  70                  75                  80

Phe Asn Val Thr Gly Ser Asp Lys Cys Val Phe Leu Lys Asn Thr Glu
                85                  90                  95

Val Ser Ser Met Glu Cys Glu Lys Asn Leu Tyr Trp Ile Cys Asn Lys
            100                 105                 110

Pro Tyr Lys
        115
```

(2) INFORMATION FOR SEQ ID NO: 9:

(i) SEQUENCE CHARACTERISTICS:
(A) LENGTH: 122 amino acids
(B) TYPE: amino acid (C) STRANDEDNESS: single
(D) TOPOLOGY: linear (ii) MOLECULE TYPE: protein (xi) SEQUENCE DESCRIPTION: SEQ ID NO: 9:

```
Cys Pro Gln Asp Trp Leu Ser His Arg Asp Lys Cys Phe His Val Ser
1               5                   10                  15

Gln Val Ser Asn Thr Trp Glu Glu Gly Leu Val Asp Cys Asp Gly Lys
            20                  25                  30

Gly Ala Thr Leu Met Leu Ile Gln Asp Gln Glu Glu Leu Arg Phe Leu
        35                  40                  45

Leu Asp Ser Ile Lys Glu Lys Tyr Asn Ser Phe Trp Ile Gly Leu Arg
    50                  55                  60

Tyr Thr Leu Pro Asp Met Asn Trp Lys Trp Ile Asn Gly Ser Thr Leu
65                  70                  75                  80

Asn Ser Asp Val Leu Lys Ile Thr Gly Asp Thr Glu Asn Asp Ser Cys
                85                  90                  95

Ala Ala Ile Ser Gly Asp Lys Val Thr Phe Glu Ser Cys Asn Ser Asp
            100                 105                 110

Asn Arg Trp Ile Cys Gln Lys Glu Leu Tyr
        115                 120
```

(2) INFORMATION FOR SEQ ID NO: 10:

(i) SEQUENCE CHARACTERISTICS:
(A) LENGTH: 129 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 10:

```
Cys Pro Val Asn Trp Val Glu Phe Gly Gly Ser Cys Tyr Trp Phe Ser
1               5                   10                  15

Arg Asp Gly Leu Thr Trp Ala Glu Ala Asp Gln Tyr Cys Gln Leu Glu
            20                  25                  30

Asn Ala His Leu Leu Val Ile Asn Ser Arg Glu Glu Gln Asp Phe Val
        35                  40                  45

Val Lys His Arg Ser Gln Phe His Ile Trp Ile Gly Leu Thr Asp Arg
    50                  55                  60

Asp Gly Ser Trp Lys Trp Val Asp Gly Thr Asp Tyr Arg Ser Asn Tyr
65                  70                  75                  80

Arg Asn Trp Ala Phe Thr Gln Pro Asp Asn Trp Gln Gly His Glu Gln
                85                  90                  95

Gly Gly Gly Glu Asp Cys Ala Glu Ile Leu Ser Asp Gly His Trp Asn
            100                 105                 110

Asp Asn Phe Cys Gln Gln Val Asn Arg Trp Val Cys Glu Lys Arg Arg
        115                 120                 125

Asn
```

(2) INFORMATION FOR SEQ ID NO: 11:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 11:

Ile Glu Gly Arg
1

(2) INFORMATION FOR SEQ ID NO: 12:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (ix) FEATURE:
(A) NAME/KEY: Peptide
(B) LOCATION: 4
(D) OTHER INFORMATION: /note= "Xaa at 1 = Leu or Ile (xi) SEQUENCE DESCRIPTION: SEQ ID NO: 12:

Tyr Xaa Xaa Xaa
1

(2) INFORMATION FOR SEQ ID NO: 13:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 13:

Tyr Ser Leu Leu
1

(2) INFORMATION FOR SEQ ID NO: 14:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 14:

Tyr Val Leu Leu
1

(2) INFORMATION FOR SEQ ID NO: 15:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 15:

Tyr Glu Asp Leu
1

(2) INFORMATION FOR SEQ ID NO: 16:

(i) SEQUENCE CHARACTERISTICS:
(A) LENGTH: 4 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO: 16:

Tyr Ser Glu Ile
1

(2) INFORMATION FOR SEQ ID NO: 17:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 17:

Tyr Ala Asp Leu
1

(2) INFORMATION FOR SEQ ID NO: 18:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 18:

Tyr Thr Thr Leu
1

(2) INFORMATION FOR SEQ ID NO: 19:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 19:

Tyr Leu Ser Leu
1

(2) INFORMATION FOR SEQ ID NO: 20:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 20:

Tyr Phe Gly Leu